United States Patent
Guy et al.

(10) Patent No.: US 10,898,462 B2
(45) Date of Patent: Jan. 26, 2021

(54) USE OF CANNABIDIOLIC ACID IN THE TREATMENT OF AUTISM SPECTRUM DISORDER AND ASSOCIATED DISORDERS

(71) Applicant: GW Research Limited, Cambridge (GB)

(72) Inventors: Geoffrey Guy, Cambridge (GB); Stephen Wright, Cambridge (GB); James Brodie, Cambridge (GB); Marie Woolley-Roberts, Cambridge (GB); Rafael Maldonado, Barcelona (ES); Daniela Parolaro, Varese (IT); Livio Luongo, Naples (IT)

(73) Assignee: GW Research Limited, Cambridge (GB)

( * ) Notice: Subject to any disclaimer, the term of this patent is extended or adjusted under 35 U.S.C. 154(b) by 0 days.

(21) Appl. No.: 16/092,560

(22) PCT Filed: Apr. 11, 2017

(86) PCT No.: PCT/GB2017/051010
§ 371 (c)(1),
(2) Date: Oct. 10, 2018

(87) PCT Pub. No.: WO2017/178810
PCT Pub. Date: Oct. 19, 2017

(65) Prior Publication Data
US 2019/0117619 A1    Apr. 25, 2019

(30) Foreign Application Priority Data
Apr. 11, 2016 (GB) .................... 1606097.2

(51) Int. Cl.
*A61K 31/352* (2006.01)
*A61K 45/06* (2006.01)
*A61K 31/05* (2006.01)
*A61K 36/185* (2006.01)
*A61P 43/00* (2006.01)

(52) U.S. Cl.
CPC ............ *A61K 31/352* (2013.01); *A61K 31/05* (2013.01); *A61K 36/185* (2013.01); *A61K 45/06* (2013.01); *A61P 43/00* (2018.01)

(58) Field of Classification Search
CPC ...... A61K 31/352; A61K 45/06; A61K 31/05; A61K 36/185
See application file for complete search history.

(56) References Cited

U.S. PATENT DOCUMENTS

| | | | | |
|---|---|---|---|---|
| 7,629,123 B2 * | 12/2009 | Millonig | ............. | C12Q 1/6883 435/6.16 |
| 9,730,911 B2 * | 8/2017 | Verzura | ................ | A61K 31/353 |
| 2015/0343071 A1 | 12/2015 | Vangara et al. | | |

FOREIGN PATENT DOCUMENTS

| | | |
|---|---|---|
| GB | 2 438 682 A | 12/2007 |
| GB | 2 434 312 B | 6/2011 |
| WO | WO 2006/017892 A1 | 2/2006 |
| WO | WO 2010/012506 A1 | 2/2010 |
| WO | WO 2015/184127 A2 | 12/2015 |
| WO | WO 2016/064987 A1 | 4/2016 |
| WO | WO 2016/071819 A2 | 5/2016 |

OTHER PUBLICATIONS

Bergamaschi, M.M. et al., "Cannabidiol Reduces the Anxiety Induced by Simulated Public Speaking in Treatment-Naïve Social Phobia Patients," Neuropsychopharmacology, vol. 36, No. 6, pp. 1219-1226 (2011).
International Search Report for International Application No. PCT/GB2017/0510107, dated Sep. 5, 2017 (three pages).
Written Opinion of the International Searching Authority for International Application No. PCT/GB2017/051010 (nine pages).

* cited by examiner

*Primary Examiner* — Sahar Javanmard
(74) *Attorney, Agent, or Firm* — Finnegan, Henderson, Farabow, Garrett & Dunner, LLP

(57) ABSTRACT

The present invention relates to the use of cannabidiolic acid (CBDA) in the treatment of autism spectrum disorder (ASD) and ASD-associated disorders, such as Fragile X syndrome (FXS); Rett syndrome (RS); or Angelman syndrome (AS). CBDA has been shown to be particularly effective in improving cognitive dysfunction in rodent models of ASD, FXS, RS and AS. The CBDA is preferably substantially pure. It may take the form of a highly purified extract of *cannabis* such that the CBDA is present at greater than 95% of the total extract (w/w) and the other components of the extract are characterised. Alternatively, the CBDA is synthetically produced.

18 Claims, 16 Drawing Sheets

Figure 1A and 1B. The effect of CBDA on sociability and social recognition deficits in the rat VPA model of general autism Figure 2A and 2B. The effect of CBDA on repetitive behaviour and hyperactivity in the rat VPA model of general autism

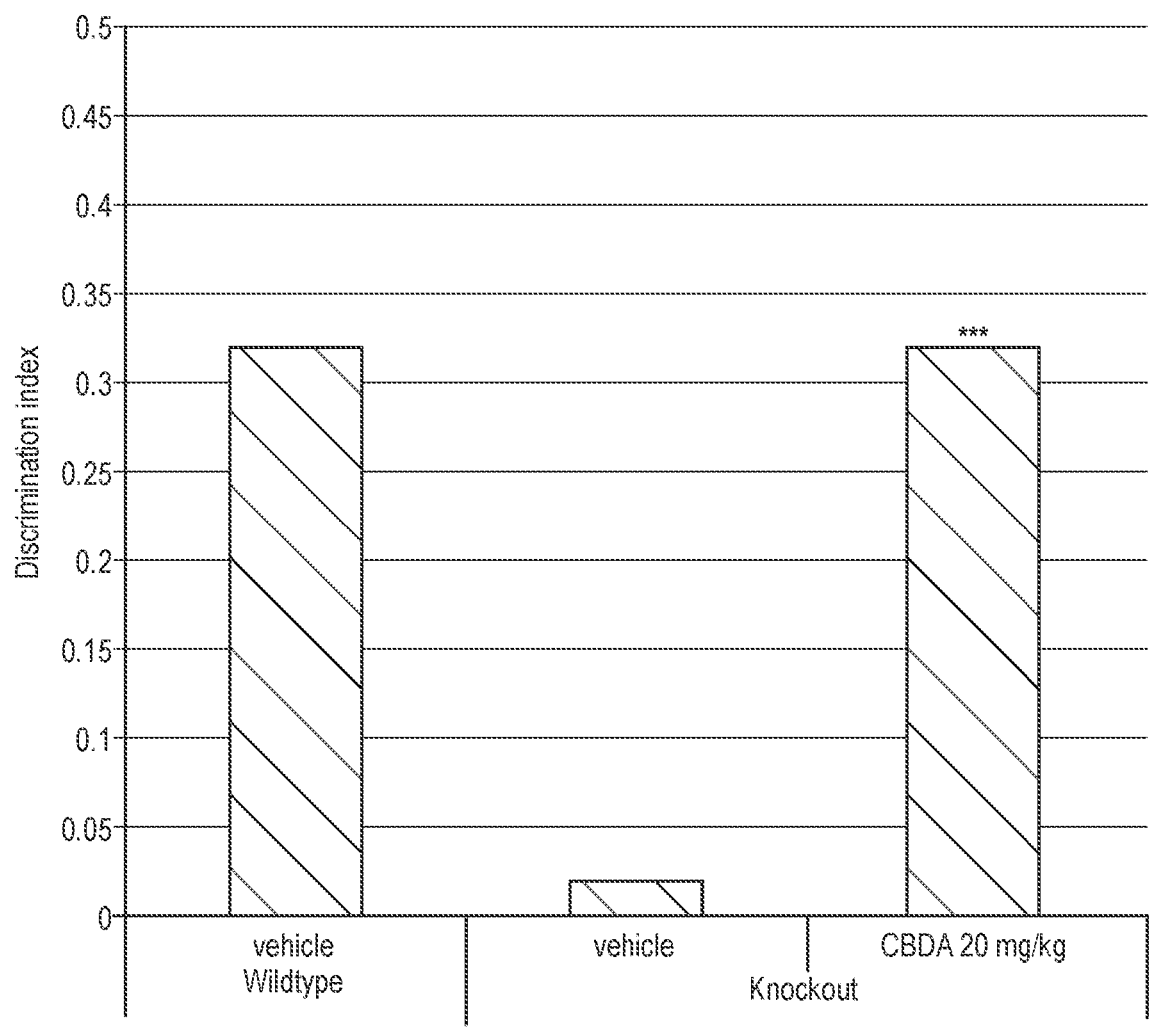
Figure 4. The effect of CBDA on discrimination index after chronic treatment in the mouse model of fragile X syndrome Figure 5A and 5B: The effect of CBDA on bodyweight in a mouse model of Rett syndrome Figure 7A-D: Effect of CBDA on symptoms in a mouse model of Rett syndrome Figure 8A-B: Effect of CBDA on symptoms in a mouse model of Rett syndrome Figure 9: Effect of CBDA on total symptom score in a mouse model of Rett syndrome Figure 10: Effect of CBDA on short-term memory in a mouse model of Rett syndrome Figure 11: Effect of CBDA on long-term memory in a mouse model of Rett syndrome Figure 12: Effect of CBDA on clasping duration in a mouse model of Angelman syndrome Figure 13: Effect of CBDA in the rotarod test in a mouse model of Angelman syndrome Figure 14: Effect of CBDA in the novel object recognition test in a mouse model of Angelman syndrome Figure 15: Effect of CBDA in the tail suspension test in a mouse model of Angelman syndrome

USE OF CANNABIDIOLIC ACID IN THE TREATMENT OF AUTISM SPECTRUM DISORDER AND ASSOCIATED DISORDERS This application is a national stage application of International Application No. PCT/GB2017/051010, filed on Apr. 11, 2017, which claims the benefit of priority of British Patent Application No. GB 1606097.2, filed on Apr. 11, 2016. The contents of these applications are each incorporated herein by reference.

FIELD OF THE INVENTION

The present invention relates to the use of cannabidiolic acid (CBDA) in the treatment of autism spectrum disorder (ASD) and ASD-associated disorders, such as Fragile X syndrome (FXS); Rett syndrome (RS); or Angelman syndrome (AS).

CBDA has been shown to be particularly effective in improving cognitive dysfunction in rodent models of ASD, FXS, RS and AS.

The CBDA is preferably substantially pure. It may take the form of a highly purified extract of cannabis such that the CBDA is present at greater than 95% of the total extract (w/w) and the other components of the extract are characterised. Alternatively, the CBDA is synthetically produced.

Alternatively the CBDA may be used as a botanical drug substance (BDS) from a cannabis plant in which CBDA is the predominant cannabinoid. The CBDA may also be present in combination with other cannabinoids and non-cannabinoid components such as terpenes.

In yet a further embodiment the CBDA may be present with one or more other cannabinoids such as CBD and/or CBDV in defined ratios in which the CBDA is the predominant cannabinoid.

In use the CBDA may be used concomitantly with one or more other medicaments. The CBDA may be formulated for administration separately, sequentially or simultaneously with one or more medicaments or the combination may be provided in a single dosage form. Where the CBDA is formulated for administration separately, sequentially or simultaneously it may be provided as a kit or together with instructions to administer the one or more components in the manner indicated. It may also be used as the sole medication, i.e. as a monotherapy.

BACKGROUND TO THE INVENTION

Autism spectrum disorder (ASD) is a condition that presents in children usually before three years of age and is characterized by a lack of social interaction, communication, interests and problems with behaviour.

The condition is relatively common as it is estimated that 1 in 100 children have some form of ASD. The condition is more prevalent in boys than girls.

In children under four the signs and symptoms of ASD include those in the area of spoken language such as delayed speech development (for example, speaking less than 50 different words by the age of two), or not speaking at all; frequent repetition of set words and phrases; speech that sounds very monotonous or flat and preferring to communicate using single words, despite being able to speak in sentences.

When responding to others these younger children will often not respond to their name being called, despite having normal hearing; reject cuddles initiated by a parent; react unusually negatively when asked to do something by someone else.

When interacting with others younger children show signs of not being aware of other people's personal space, or being unusually intolerant of people entering their own personal space; little interest in interacting with other people, including children of a similar age; not enjoying situations that most children of their age like, such as birthday parties; preferring to play alone, rather than asking others to play with them; rarely using gestures or facial expressions when communicating; and avoiding eye contact.

Symptoms involving behaviour in pre-school children include: having repetitive movements, such as flapping their hands, rocking back and forth, or flicking their fingers; playing with toys in a repetitive and unimaginative way, such as lining blocks up in order of size or colour, rather than using them to build something; preferring to have a familiar routine and getting very upset if there are changes to this routine; having a strong like or dislike of certain foods based on the texture or colour of the food as much as the taste; and unusual sensory interests for example, children with ASD may sniff toys, objects or people inappropriately.

In older school age children some of the signs and symptoms of ASD are similar to those experienced by younger children and also include other symptoms. With spoken language an older child with ASD often prefers to avoid using spoken language; has speech that sounds very monotonous or flat; may speak in pre-learned phrases, rather than putting together individual words to form new sentences; may seem to talk "at" people, rather than sharing a two-way conversation.

When responding to others, school age children with ASD often take people's speech literally and are unable to understand sarcasm, metaphors or figures of speech they may also react unusually negatively when asked to do something by someone else.

When interacting with others school age children with ASD may not be aware of other people's personal space, or are unusually intolerant of people entering their own personal space; show little interest in interacting with other people, including children of a similar age, or have few close friends, despite attempts to form friendships; not understand how people normally interact socially, such as greeting people or wishing them farewell; are unable to adapt the tone and content of their speech to different social situations for example, speaking very formally at a party and then speaking to total strangers in a familiar way; not enjoy situations and activities that most children of their age enjoy; rarely use gestures or facial expressions when communicating; and avoid eye contact.

With respect to the problems with behaviour that older children with ASD experience these include repetitive movements, such as flapping their hands, rocking back and forth, or flicking their fingers; playing in a repetitive and unimaginative way, often preferring to play with objects rather than people; developing a highly specific interest in a particular subject or activity; preferring to have a familiar routine and getting very upset if there are changes to their normal routine; having a strong like or dislike of certain foods based on the texture or colour of the food as much as the taste; unusual sensory interests for example, children with ASD may sniff toys, objects or people inappropriately.

According to DSM-IV autism is diagnosed with three core characteristics using the following criteria: A total of six (or more) items from lists (1), (2), and (3), with at least two items from list (1), and one item from each of lists (2) and (3).

List (1) qualitative impairment in social interaction, as manifested by at least two of the following:
  a. marked impairment in the use of multiple nonverbal behaviors, such as eye-to-eye gaze, facial expression, body postures, and gestures to regulate social interaction;
  b. failure to develop peer relationships appropriate to developmental level;
  c. a lack of spontaneous seeking to share enjoyment, interests, or achievements with other people (e.g., by a lack of showing, bringing, or pointing out objects of interest); and
  d. lack of social or emotional reciprocity.

List (2) qualitative impairments in communication, as manifested by at least one of the following:
  a. delay in, or total lack of, the development of spoken language (not accompanied by an attempt to compensate through alternative modes of communication such as gesture or mime);
  b. in individuals with adequate speech, marked impairment in the ability to initiate or sustain a conversation with others;
  c. stereotyped and repetitive use of language or idiosyncratic language; and
  d. lack of varied, spontaneous make-believe play or social imitative play appropriate to developmental level.

List (3) restricted, repetitive, and stereotyped patterns of behaviour, interests, and activities as manifested by at least one of the following:
  a. encompassing preoccupation with one or more stereotyped and restricted patterns of interest that is abnormal either in intensity or focus;
  b. apparently inflexible adherence to specific, non-functional routines or rituals;
  c. stereotyped and repetitive motor mannerisms (e.g., hand or finger flapping or twisting or complex whole-body movements); and
  d. persistent preoccupation with parts of objects.

According to DSM-V which was published in May 2013, the new diagnostic criteria for autism spectrum disorder is that the patient must either currently, or by history, meet criteria from all of A, B, C, and D.

A. Persistent deficits in social communication and social interaction across contexts, not accounted for by general developmental delays, and manifest by all 3 of the following:
  a. Deficits in social-emotional reciprocity; which may range for example from abnormal social approach and failure of normal back and forth conversation, to reduced sharing of interest, emotions, or affect, to failure to initiate or respond;
  b. Deficits in communicative behaviours used for social interaction; ranging for example, from poorly integrated verbal and non-verbal communication, to abnormalities in eye contact and body language or deficits in understanding and use of gestures, to a total lack of facial expressions and non-verbalisation; and
  c. Deficits in developing, maintaining and understanding relationships, ranging for example from difficulties adjusting behaviour to suit various social contexts, difficulties in sharing imaginative play or in making friends, to absence of interest in peers.

B. Restricted, repetitive patterns of behaviour, interests, or activities as manifested by at least two of the following:
  a. Stereotyped or repetitive motor movements, use of objects, or speech, (such as simple motor stereotypies, lining up toys or flipping plates, echolalia, idiosyncratic phrases);
  b. Insistence on sameness, inflexible adherence to routines, or ritualized patterns of verbal or non-verbal behaviour (such as extreme distress at small changes, difficulties with transitions, rigid thinking patterns, greeting rituals, need to take same route or eat same food every day);
  c. Highly restricted, fixated interests that are abnormal in intensity or focus (such as strong attachment to or preoccupation with unusual objects, excessively circumscribed or perseverative interests); and
  d. Hyper- or hypo-reactivity to sensory input or unusual interest in sensory aspects of the environment (such as apparent indifference to pain/temperature, adverse response to specific sounds or textures, excessive smelling or touching of objects, visual fascination with lights or movement).

C. Symptoms must be present in early childhood but may not become fully manifest until social demands exceed limited capacities.

D. Symptoms together limit and impair everyday functioning.

In certain genetic syndromes there is a strong prevalence of ASD or characteristics of ASD. Such syndromes can be said to be ASD-associated disorders. Such genetic syndromes include: Tuberous Sclerosis Complex, Fragile X syndrome, Cornelia de Lange syndrome, Down syndrome, Angelman syndrome, Coffin-Lowry syndrome, Cohen Laurence-Moon-Biedel syndrome, Marinesco-Sjogren syndrome, Moebius syndrome, Phelan-McDermid syndrome, CDKLS, Dup15q, Potocki-Lupski syndrome, Smith Lemli Optiz syndrome, Timothy syndrome, Prader-Willi syndrome, Rett syndrome and Williams syndrome.

It has been suggested that the genes underlying those syndromes in which ASD characteristics are very common, lead to common differences at the biological and neurological level, which in turn give rise to the presentation of ASD characteristics.

Fragile X syndrome (FXS) co-occurs with autism in many cases and is the most common cause of inherited learning disability, occurring in 1 in 3,600 males and 1 in 8,000 females. FXS is caused by the presence of an apparently unstable or 'fragile' site located on the FMR1 gene on the X chromosome. The instability is caused by an excess of genetic code in this region. Males with FXS typically show mild to severe learning disability while females with FXS usually have a mild learning disability.

Recent studies of individuals with FXS show a fairly consistent pattern of association with ASD. The percentage of individuals with FXS showing ASD characteristics or meeting ASD criteria is up to 50%. Severe ASD is relatively rare in FXS and a milder presentation of ASD-like features is more characteristic.

Impairments in social interaction in FXS are characterised by social anxiety, extreme shyness and eye gaze avoidance. These characteristics are also observed in individuals with ASD. The social impairments associated with FXS often increase as the patient gets older.

The major symptom of FXS is intellectual disability with an average IQ of 40 in males who have complete silencing of the FMR1 gene. The main difficulties in individuals with FXS are with working and short-term memory, executive function, visual memory, visual-spatial relationships, and mathematics, with verbal abilities being relatively spared.

FXS sufferers also present with prominent characteristics which may include an elongated face, large or protruding ears, flat feet, larger testes (macro-orchidism), and low muscle tone.

FXS patients also suffer from recurrent middle ear infection and sinusitis. Speech may be cluttered or nervous. Behavioural characteristics may include stereotypic movements such as hand-flapping and atypical social development, particularly shyness, limited eye contact, memory problems, and difficulty with face encoding. These features mean that individuals with FXS also meet the diagnostic criteria for autism. Genetic mouse models of FXS have also been shown to have autistic-like behaviours.

Attention deficit hyperactivity disorder (ADHD) is found in the majority of males with FXS and 30% of females, making it the most common psychiatric diagnosis in those with FXS. Hyperactivity and disruptive behaviour peak in the preschool years and then gradually decline with age, although inattentive symptoms are generally lifelong.

From their 40s onward, males with FXS begin developing progressively more severe problems in performing tasks that require the central executive of working memory.

There is currently no drug treatment that has shown benefit specifically for FXS. However, medications are commonly used to treat symptoms of attention deficit and hyperactivity, anxiety, and aggression.

Rett syndrome (RS) is a neurological disorder that is caused by a mutation on the X chromosome. RS predominantly affects females and occurs in 1 in 15,000 to 22,800 live female births. Typically, development appears to be normal in the first six to eighteen months but this is followed by a period of regression resulting in a loss of language and motor skills, leading to severe or profound learning and physical disabilities.

Autistic-like behaviours were noted in the very first description of RS in 1966. Studies have since estimated that 25% to 40% of individuals with RS show ASD-like characteristics. ASD is the most common misdiagnosis in children with RS, with many individuals being diagnosed with ASD prior to receiving a diagnosis of RS.

RS is caused by a mutation in the MECP2 gene which is found on the X chromosome. The MECP2 gene codes for the MeCP2 protein which is essential for brain development. Without this protein nerve cells in the brain are prevented from developing properly.

The symptoms associated with RS usually go unnoticed for the first few months of a child's life. The symptoms then tend to progress over several stages as outlined below.

Stage one consists of early signs and slow development, these usually appear in the first six to twelve months of the child's life. The symptoms include: a general slowness in development; hypertonia; difficulty feeding; abnormal hand movements; lack of interest in toys; and poor coordination of trunk and limbs.

Stage two is known as the regression or rapid destruction stage. This stage usually begins between the age of one and four and may last for weeks or months. The child will develop severe cognitive impairment. Problems arise with communication, language, learning, co-ordination and brain functions. Signs at this stage include: repetitive and uncontrollable hand movements; periods of distress, irritability and screaming; social withdrawal; unsteadiness when walking; rapid or slow breathing; problems sleeping; small head size; difficulty eating and gastrointestinal problems.

Many children with RS also start to suffer from epileptic seizures at this stage; up to 80% of children with the syndrome suffer from epilepsy at some stage of their illness.

Stage three is known as the plateau stage and usually begins between the ages of two and ten. This stage can last for years indeed many RS sufferers will remain in this stage for the majority of their life. The prominent symptoms include: floppiness of limbs and inability to move around; inability to use hands to hold, carry or manipulate objects; repetitive hand movements; teeth grinding; abnormal tongue movements; and lack of gain in bodyweight.

The final stage is characterized by deterioration in movement. This stage can again last for years or even decades. The main problems are caused by scoliosis of the spine; spasticity and loss of the ability to walk.

The lifespan of a child born with RS is generally shortened often due to life threatening seizures or arrhythmias.

There is no cure for RS however anti-epileptic medications are often prescribed to control the seizures along with a high calorie diet and physiotherapy to help control the symptoms.

Angelman syndrome (AS) occurs in approximately 1 in 12,000 to 15,000 individuals and is caused by abnormalities on chromosome 15. Individuals with AS typically show severe to profound learning disability, significant difficulties with mobility and communication in addition to seizures.

It has been suggested that between 50% and 80% of individuals with AS meet the criteria for ASD.

Typical characteristics of Angelman syndrome include: delayed development which is usually noticeable from 6-12 months of age; severe language impairment with little or no speech; movement and balance problems (ataxia); frequent seizures (epilepsy) in around 85% of cases; a small head size (microcephaly); sociable behaviour with frequent smiling.

A genetic anomaly responsible for AS which occurs by chance around the time of conception. The UBE3A gene is either absent or malfunctions. A child usually inherits one copy of the UBE3A gene from each parent. Both copies are switched on (active) in most of the body's tissues. However, in certain areas of the brain, only the gene inherited from the mother is active. In most cases of AS (about 70%), the child's maternal copy of the UBE3A gene is missing, which means there's no active copy of the UBE3A gene in the child's brain.

Testing compounds for their effectiveness on signs and symptoms of ASD and ASD-associated disorders is challenging given that these disorders have so many different affected symptom domains.

The rodent valproic acid model is a widely accepted model of ASD. Rat foetuses are exposed to valproic acid on the 12.5th day of gestation to produce VPA rats. The VPA rats present behavioural aberrations observed in autism such as delayed maturation, lower body weight, delayed motor development, and attenuated integration of a coordinated series of reflexes, delayed nest-seeking response mediated by olfactory system, and normal negative geotaxis.

Additionally there are particular animal models which can be used to test particular syndromes which present with ASD like characteristics such as FXS, RS and AS or ASD-associated disorders.

Male patients with FXS lack the FMR1 protein due to silencing of the FMR1 gene by amplification of a CGG repeat and subsequent methylation of the promoter region. A knockout model for FXS in mice is a well-known model used to test compounds for their effectiveness in the treatment of FXS. Mice lack normal FMR1 protein and show macro-orchidism, learning deficits, and hyperactivity.

The MeCP2 knockout mouse model is able to evaluate the effectiveness of a treatment the symptoms that present in RS. Mice lacking the MeCP2 gene show severe neurological symptoms at approximately six weeks of age. After several months, heterozygous female mice also show autism like behavioural symptoms.

The UBE3A mouse model is used to evaluate a compounds effectiveness in the treatment of AS. This model has been shown to recapitulate many of the phenotypic features of AS, including motor dysfunction, increased seizure susceptibility, and hippocampal-dependent learning and memory deficits in mice with the knockout gene.

The NOR test is used to evaluate cognition, particularly recognition memory, in rodent models of CNS disorders, such as ASD and ASD-associated disorders. The test is based on the tendency of rodents to spend more time exploring a novel object than a familiar one. The choice to explore the novel object reflects the use of learning and recognition memory.

The NOR test is conducted in an open field arena with two different kinds of objects. Both objects are generally consistent in height and volume, but are different in shape and appearance. During habituation, the animals are allowed to explore an empty arena. Twenty-four hours after habituation, the animals are exposed to the familiar arena with two identical objects placed at an equal distance. The next day, the mice are allowed to explore the open field in the presence of the familiar object and a novel object to test short-term and long-term recognition memory. The time spent exploring each object and the discrimination index percentage is recorded. This test is useful for assessing cognitive dysfunction in rodent models of ASD, FXS, RS and AS.

The Food and Drug Administration (FDA) has approved two drugs for treating irritability associated with the autism (risperidone and aripiprazole) which are both antipsychotic medications. However, there are currently no approved medications for treating autism's core characteristics. Antipsychotics can ease core symptoms to some extent, for example relieving irritability often improves sociability, reduces tantrums, aggressive outbursts and self-injurious behaviour. The disadvantages associated with antipsychotics are that this class of medicaments known to have side effects including severe weight gain, stiffness and shakiness. Accordingly it would be desirable to provide a more effective medication able to treat the core characteristics of ASD in addition to a better side effect profile.

The endocannabinoid system has been linked to physiological progression of autism spectrum disorders, possibly implicating CB1 and CB2 receptors.

The phytocannabinoids are known to interact with the endocannabinoid system.

The phytocannabinoid tetrahydrocannabinol (THC) in the form of dronabinol, a CB1 agonist, has been used to treat an autistic child (Kurz and Blass, 2010). Problems associated with the use of CB1 agonists are psychoactivity, anxiety and hallucinations.

Patent application WO 2010/012506 describes the use of cannabinoids in the treatment of dementia and GB 2,434,312 describes the use of cannabinoids in the treatment of neurodegenerative diseases and disorders.

Patent application WO 2014/146699 describes the use of CB1 receptor antagonists in the treatment of diseases associated with dendritic abnormalities. Such diseases include AS and RS. The application is exemplified by the use of rimonabant in the FMR1 knockout mouse model which is a model of FXS.

The CB1 antagonist, rimonabant, has been shown to have serious side effects such as suicide ideation which limit its use.

The present application relates to the use of a phytocannabinoid which is neither a CB1 agonist nor antagonist. Cannabidiolic acid (CBDA) is the un-decarboxylated form of cannabidiol (CBD) and little is known about the binding affinities of this compound. It is however likely to act at the CB1 receptors in a similar manner to the decarboxylated compound CBD which is known to have a low affinity for the CB1 receptor (Mechoulam et al. 2007).

In the co-pending UK patent application GB1514079.1, CBDA has been shown to be effective in animal models of seizure. This patent application also demonstrates that CBDA is more bioavailable than CBD.

To date there are no studies of the use of CBDA in the treatment of ASD or ASD-associated disorders such as FXS, RS and AS. Such symptoms as described above are difficult to treat, therefore many patients with ASD and ASD-associated disorders such as FXS, RS and AS have unmet needs with respect to the treatment of their disease.

BRIEF SUMMARY OF THE DISCLOSURE

In accordance with a first aspect of the present invention there is provided Cannabidiolic acid (CBDA) for use in the treatment of one or more symptoms or disease characteristics associated with autistic spectrum disorder (ASD) or ASD-associated disorders, as defined by DSM-IV, wherein the symptoms or disease characteristic is one or more selected from the group consisting of: (i) qualitative impairment in social interaction; (ii) qualitative impairment in communication; and (iii) restricted repetitive and stereotyped patterns of behaviour interest and activities.

Preferably the symptoms or disease characteristics of qualitative impairment in social interaction include one or more of: (a) marked impairment in the use of multiple nonverbal behaviours, such as eye-to-eye gaze, facial expression, body postures, and gestures to regulate social interaction; (b) failure to develop peer relationships appropriate to developmental level; (c) a lack of spontaneous seeking to share enjoyment, interests, or achievements with other people (e.g., by a lack of showing, bringing, or pointing out objects of interest); and (d) lack of social or emotional reciprocity.

Preferably the symptoms or disease characteristics of qualitative impairment in communication include one or more of: (a) delay in, or total lack of, the development of spoken language (not accompanied by an attempt to compensate through alternative modes of communication such as gesture or mime); (b) in individuals with adequate speech, marked impairment in the ability to initiate or sustain a conversation with others; (c) stereotyped and repetitive use of language or idiosyncratic language; and (d) lack of varied, spontaneous make-believe play or social imitative play appropriate to developmental level.

Preferably the symptoms or disease characteristics of restricted repetitive and stereotyped patterns of behaviour interest and activities include one or more of: (a) encompassing preoccupation with one or more stereotyped and restricted patterns of interest that is abnormal either in intensity or focus; (b) apparently inflexible adherence to specific, nonfunctional routines or rituals; (c) stereotyped and repetitive motor mannerisms (e.g., hand or finger flapping or twisting or complex whole-body movements); and (d) persistent preoccupation with parts of objects.

Preferably the symptoms or characteristics associated with of autistic spectrum disorder comprise at least two symptoms associated with qualitative impairment in social interaction; at least one symptom associated with qualitative impairment in communication and at least one symptom associated with restricted repetitive and stereotyped patterns of behaviour interest and activities.

In accordance with a second aspect of the present invention there is provided Cannabidiolic acid (CBDA) for use in the treatment of autistic spectrum disorder (ASD) or ASD-associated disorders as defined by DSM-V, wherein the symptoms or disease characteristic is one or more selected from the group consisting of: (a) persistent deficits in social communication and social interaction across contexts, not accounted for by general developmental delays, and (b) restricted, repetitive patterns of behaviour, interests, or activities.

Preferably the symptoms or disease characteristics of (a) persistent deficits in social communication and social interaction across contexts, not accounted for by general developmental delays include one or more of: (i) deficits in social-emotional reciprocity; (ii) deficits in nonverbal communicative behaviours used for social interaction; and (iii) deficits in developing and maintaining relationships.

Preferably the symptoms or disease characteristics of (b) restricted, repetitive patterns of behaviour, interests, or activities include one or more of: (i) stereotyped or repetitive speech, motor movements, or use of objects; excessive adherence to routines, (ii) ritualized patterns of verbal or nonverbal behaviour, or excessive resistance to change; (iii) highly restricted, fixated interests that are abnormal in intensity or focus; and (iv) hyper-or hypo-reactivity to sensory input or unusual interest in sensory aspects of environment.

Preferably the symptoms or disease characteristics associated with of autistic spectrum disorder comprise all three symptoms associated with (a) persistent deficits in social communication and social interaction across contexts, not accounted for by general developmental delays together with at least two of (b) restricted, repetitive patterns of behaviour, interests, or activities.

In this aspect, treatment of ASD and ASD-associated disorders encompass the treatment of the condition as a whole as opposed to the individual symptoms. Accordingly the present invention does not encompass CBDA for use in the treatment of seizures.

Preferably the ASD-associated disorder is taken from the group: Fragile X syndrome; Rett syndrome or Angelman syndrome.

In accordance with a third aspect of the present invention there is provided Cannabidiolic acid (CBDA) for use in the treatment of cognitive dysfunction.

Preferably the CBDA is for use in the treatment of short-term and/or long-term memory in ASD or ASD-associated disorders.

In a further embodiment the CBDA is for use in combination with one or more concomitant medicaments which may be taken by the patient to treat the condition and/or one or more symptoms associated therewith. Such as, for example, melatonin for sleeping problems, SSRI for depression, anticonvulsants for epilepsy, methylphenidate for ADHD or antipsychotics for aggression or self-harming behaviour. In this respect CBDA is not used to treat seizures.

Preferably the one or more concomitant medicaments is an anti-epileptic drug (AED). The AED may be the cannabinoid CBD and as such a combination of CBDA and CBD may be used.

In a further embodiment the CBDA is substantially pure. The CBDA may be present as a highly purified extract of cannabis which comprises at least 95% (w/w) CBDA. Preferably the extract comprises less than 0.15% THC and/or tetrahydrocannabinolic acid (THCA).

In an alternative embodiment the CBDA is present as a synthetic compound.

Alternatively the CBDA may be used as an extract from a cannabis plant in which CBDA is the predominant cannabinoid. The CBDA may also be present in combination with other cannabinoids and non-cannabinoid components such as terpenes.

In yet a further embodiment the CBDA may be present with one or more other cannabinoids such as CBD and/or CBDV in defined ratios in which the CBDA is the predominant cannabinoid.

Determining an effective dose in humans will depend on, for example the mode of delivery (i.v. or oral), the formulation and the bioavailability of the CBDA when delivered and might range between 0.1 and 100 mg/kg/day. Furthermore the fact that cannabinoids often show bell-shaped dose response curves makes determining a dose of CBDA more difficult.

CBDA is known to be more bioavailable than its decarboxylated form CBD.

Preferably the dose of CBDA is greater than 0.01 mg/kg/day. Thus for a 15 kg patient a dose of greater than 0.15 mg of CBDA per day would be provided. Doses greater than 0.1 mg/kg/day, such as greater than 1 mg/kg/day, such as greater than 5 mg/kg/day, greater than 10 mg/kg/day, greater than 15 mg/kg/day and greater than 20 mg/kg/day are also envisaged to be effective.

In use the CBDA may be effective in a therapeutic amount of between 1 to 30 mg/kg/day and it may also be administered as an oral formulation.

Preferably the CBDA is provided over an extended period; more preferably this period is at least seven days.

In a further embodiment the CBDA may be used as a dietary supplement or food additive in order to improve symptoms in ASD or ASD-associated conditions.

In accordance with a fourth aspect of the present invention there is provided a method of treating one or more symptoms or disease characteristics associated with autistic spectrum disorder (ASD) or ASD-associated disorders in a subject, as defined by DSM-IV, wherein the symptoms or disease characteristic is one or more selected from the group consisting of: qualitative impairment in social interaction; qualitative impairment in communication; and restricted repetitive and stereotyped patterns of behaviour interest and activities, comprising administering an effective amount of cannabidiolic acid (CBDA) to the subject in need thereof. Preferably the subject is a human.

In accordance with a fifth aspect of the present invention there is provided a method of treating one or more symptoms or disease characteristics associated with autistic spectrum disorder (ASD) or ASD-associated disorders in a subject, as defined by DSM-V, wherein the symptoms or disease characteristic is one or more selected from the group consisting of: (a) persistent deficits in social communication and social interaction across contexts, not accounted for by general developmental delays, and (b) restricted, repetitive patterns of behaviour, interests, or activities, comprising administering an effective amount of cannabidiolic acid (CBDA) to the subject in need thereof. Preferably the subject is a human.

Preferably the ASD-associated disorder is taken from the group: Fragile X syndrome; Rett syndrome or Angelman syndrome.

In accordance with a sixth aspect of the present invention there is provided a method of treating cognitive dysfunction in a subject comprising administering an effective amount of cannabidiolic acid (CBDA) to the subject in need thereof. Preferably the subject is a human.

The human dose equivalent (H ED) can be estimated using the following formula:

$$HED = \text{Animal dose (mg/kg) multiplied by } \frac{\text{Animal } K_m}{\text{Human } K_m}$$

The $K_m$ for a mouse is 3, for a rat the $K_m$ is 6 and the $K_m$ for a human is 37.

Definitions

Definitions of some of the terms used to describe the invention are detailed below:

The cannabinoids described in the present application are listed below along with their standard abbreviations.

nabinoids and Synthetic cannabinoids (which may be novel cannabinoids or synthetically produced phytocannabinoids or endocannabinoids).

"Phytocannabinoids" are cannabinoids that originate from nature and can be found in the cannabis plant. The phytocannabinoids can be isolated from plants to produce a highly purified extract or can be reproduced synthetically.

"Substantially pure CBDA" is defined as CBDA that is greater than 95% (w/w) pure. More preferably greater than 96% (w/w) through 97% (w/w) through 98% (w/w) to 99% (w/w) and greater.

"Highly purified cannabinoid extracts" are defined as cannabinoids that have been extracted from the cannabis plant and purified to the extent that other cannabinoids and non-cannabinoid components that are co-extracted with the cannabinoids have been substantially removed, such that the highly purified cannabinoid is greater than or equal to 98% (w/w) pure.

"Botanical drug substance" or "(BDS)" is defined in the Guidance for Industry Botanical Drug Products Draft Guid-

TABLE 1

Cannabinoids and their abbreviations

CBD    Cannabidiol

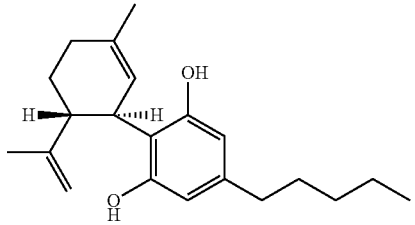 [SMILES: C=C(C)[C@@H]1CCC(C)=C[C@H]1c1c(O)cc(CCCCC)cc1O]

CBDA   Cannabidiolic acid

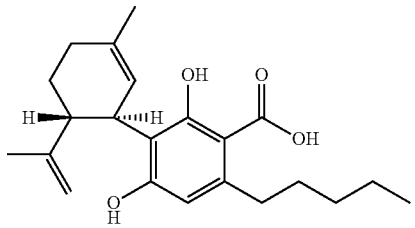 [SMILES: C=C(C)[C@@H]1CCC(C)=C[C@H]1c1c(O)cc(CCCCC)c(C(=O)O)c1O]

THC    Tetrahydrocannabinol

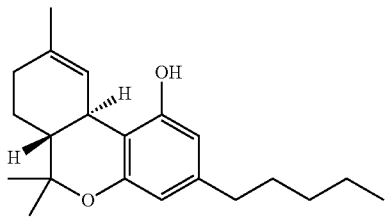 [SMILES: CCCCCc1cc(O)c2c(c1)OC(C)(C)[C@@H]1CCC(C)=C[C@@H]21]

THCA   Tetrahydrocannabinolic acid

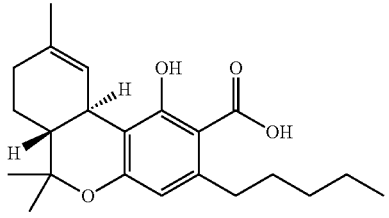 [SMILES: CCCCCc1cc2c(c(O)c1C(=O)O)[C@@H]1C=C(C)CC[C@H]1C(C)(C)O2]

The table above is not exhaustive and merely details the cannabinoids which are identified in the present application for reference. So far over 60 different cannabinoids have been identified and these cannabinoids can be split into different groups as follows: Phytocannabinoids; Endocanance, August 2000, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes."
A botanical drug substance does not include a highly purified or chemically modified substance derived from natural sources. Thus, in the case of cannabis, BDS derived from cannabis plants do not include highly purified Pharmacopoeial grade cannabinoids. In a BDS comprising cannabinoids the cannabinoid will be present in an amount of less than 95% (w/w).

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

"Cognitive dysfunction" is defined as the loss of intellectual functions such as thinking, remembering, and reasoning with sufficient severity to interfere with daily functioning. Patients with cognitive dysfunction have trouble with verbal recall, basic arithmetic, and concentration.

An ASD-associated disorder is defined as genetic syndromes where there is a strong prevalence of ASD or characteristics of ASD. Such genetic syndromes include: Tuberous Sclerosis Complex, Fragile X syndrome, Cornelia de Lange syndrome, Down syndrome, Angelman syndrome, Coffin-Lowry syndrome, Cohen Laurence-Moon-Biedel syndrome, Marinesco-Sjogren syndrome, Moebius syndrome, Phelan-McDermid syndrome, CDKLS, Dup15q, Potocki-Lupski syndrome, Smith Lemli Optiz syndrome, Timothy syndrome, Prader-Willi syndrome, Rett syndrome and Williams syndrome.

A symptom or disease characteristic associated with ASD or ASD-associated disorders are defined as the diagnostic criteria as defined by either DSM-IV or DSM-V as described above (under the section "Background to the Invention").

BRIEF DESCRIPTION OF THE DRAWINGS

Embodiments of the invention are further described hereinafter with reference to the accompanying drawings, in which

FIG. 4 shows the effect of CBDA on discrimination index after chronic treatment in the mouse model of fragile X syndrome;

Figure 1A:
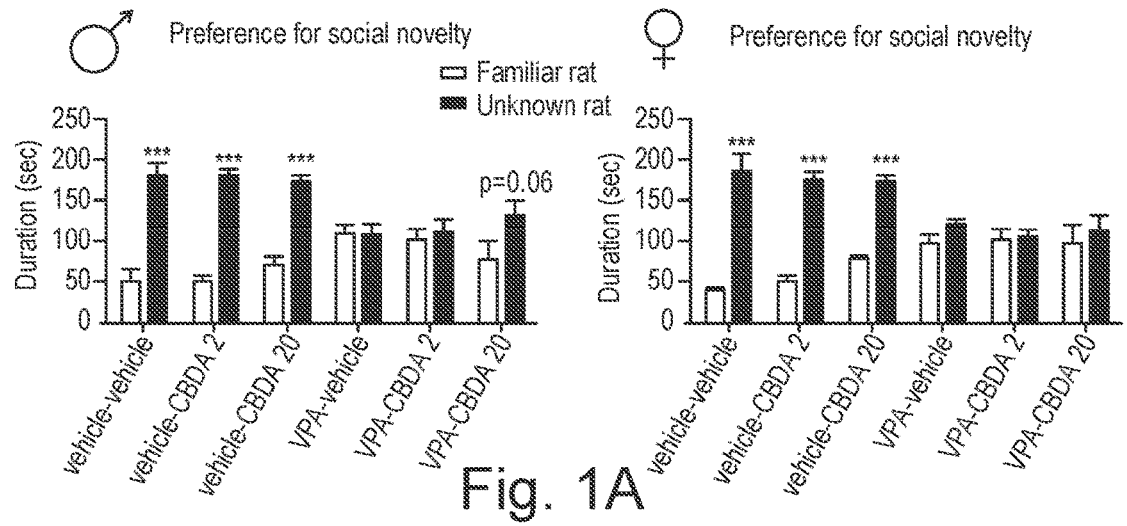
FIG. 1A-C shows the effect of CBDA on sociability and social recognition deficits in the rat VPA model of general autism.

For all figures data are expressed as mean±S.E.M. *$p<0.05$,***$p<0.001$ vs WT-vehicle; ° ° $p<0.01$,° ° ° $p<0.001$ vs KO-vehicle. Two-way ANOVA followed by Bonferroni post hoc test.

DETAILED DESCRIPTION

Example 1

Use of Cannabidiolic Acid (CBDA) in a Mouse Model of Autism Spectrum Disorder

The phytocannabinoid cannabidiolic acid (CBDA) was evaluated in a rodent model of autism spectrum disorder (ASD).

In utero exposure of rodents to valproic acid (VPA) has been shown to induce a phenotype with behavioural characteristics similar to those observed in ASD and provides a robust animal model for social cognitive impairment understanding and a potential screen for the development of novel therapeutics for this condition (Foley et al. 2012).

Thus, in utero exposure to VPA has been used as a reliable model to increase the understanding of behavioural effects evaluated by specific tests as sociability, social preference and stereotypic behaviour, also observed in human patients (Schneider and Przewlocki, 2005).

Example 1 describes the use of prenatal VPA exposure in rats to evaluate the efficacy of chronic CBDA administration in reversing the autism-like behaviours present in this model.

Materials and Methods

Prenatal VPA Administration

Pregnant Sprague-Dawley rats (Charles River, Calco, Italy), received a single intraperitoneal injection of 500 mg/kg sodium valproate on the 12.5 day after conception, and control females were injected with physiological saline at the same time. Sodium valproate (Sigma Aldrich, Milan, IT) was dissolved in saline at a concentration of 250 mg/ml.

Females were housed individually and were allowed to raise their own litters. The offspring was weaned on postnatal day (PND) 21, separated by sex and the animals were kept four to a cage, with controlled temperature and light conditions. Rats had free access to food (standard laboratory pellets) and water. All the experiments were performed in the light phase between 09:00 and 15:00.

CBDA Treatment

CBDA was dissolved in ethanol, cremophor and saline (1:1:18). Symptomatic treatment with CBDA at doses of 2 and 20 mg/kg/day i.p. was performed starting from PND 34 (early adolescence) till 56 (early adulthood), both in male and female offspring of dams injected with VPA 500 mg/kg (or vehicle) on day 12.5 after conception. At PND 56, a series of behavioural tests was performed in order to assess the effect of chronic CBDA on sociability, social novelty, short-term memory, locomotion and stereotyped/repetitive behaviours.

Behavioural Studies

Locomotor activity and repetitive behaviours: Locomotor activity was recorded in an activity cage for 20 minutes with the aid of Anymaze program (Ugo Basile, Italy). In this period, repetitive behaviours (self-grooming and digging) were measured by an observer blind to the treatment group.

Sociability and preference for social novelty: These behaviours were investigated in a 3-chamber apparatus which allows for the measurement of social approach and social preference. In brief, animals were placed into a novel arena (80 cm×31.5 cm) composed of three communicating chambers separated by Perspex walls with central openings allowing access to all chambers for 5 min.

Distance moved (m) and time spent (s) in the various compartments was assessed during this time to evaluate general locomotor activity and ensure that animals did not have a preference for a particular side of the arena.

Following this acclimatisation period, animals were briefly confined to the central chamber while an unfamiliar rat confined in a small wire cage was placed in one of the outer chambers. An identical empty wire cage was placed in the other chamber. The unfamiliar rat was randomly assigned to either the right or left chamber of the arena. The test animal was then allowed to explore the arena/chambers for a further 5 min. Time spent engaging in investigatory behaviour with the rat was evaluated with the aid of Anymaze program (Ugo Basile, Italy) in order to examine social approach.

To investigate the preference for social novelty, a novel unfamiliar rat was then placed in the empty cage and the test animal was then allowed to explore the arena/chambers for a further 5 min. Time spent engaging in investigatory behaviour with the novel unfamiliar rat was evaluated with the aid of Anymaze program (Ugo Basile, Italy) in order to examine preference for social novelty.

Short-term memory: The experimental apparatus used for the object recognition test was an open-field box (43×43×32 cm) made of Plexiglas, placed in a dimly illuminated room. The experiment was performed and analysed as previously described (Zamberletti et al, 2014). Animals performed each test individually.

Each animal was placed in the arena and allowed to explore two identical previously unseen objects for 5 minutes (familiarization phase). After an inter-trial interval of 3 minutes one of the two familiar objects was replaced by a novel, previously unseen object and rats were returned to the arena for the 5-minute test phase. During the test phase the time spent exploring the familiar object (Ef) and the new object (En) was videotaped and recorded separately by two observers blind to the treatment groups and the discrimination index was calculated as follows: $[(En-Ef)/(En+Ef)] \times 100$.

Statistical analysis: Data were expressed as mean±. Results were analysed by unpaired Student's t test or two-way ANOVA, followed up by Bonferroni's post hoc test. The level of statistical significance was set at $p<0.05$.

Results

FIG. 1A shows the effect of the two different doses of CBDA treatment on social novelty preference in offspring of VPA- and vehicle-exposed rats, as measured through the three chamber apparatus. CBDA at 20 mg/kg was demonstrated to have a statistically significant effect in males on restoration of social novelty preference.

During the habituation phase, no differences in the time spent in each compartment of the maze were observed, suggesting that animals did not show a preference for a particular side of the arena (data not shown).

During the sociability test, two-way ANOVA revealed significant main effects of VPA and CBDA on sociability. VPA-exposed rats spent significantly less time in the chamber containing the unfamiliar rat with respect to the time spent in the empty compartment when compared to controls.

Figure 1B:
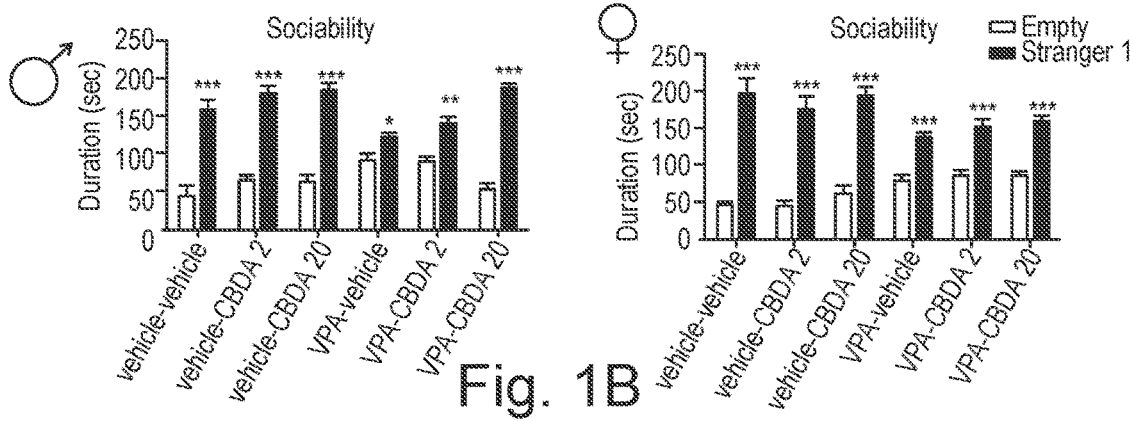

FIG. 1B shows that CBDA treatment at both doses significantly reduced the impairment in sociability observed in VPA rats.

Figure 1C:
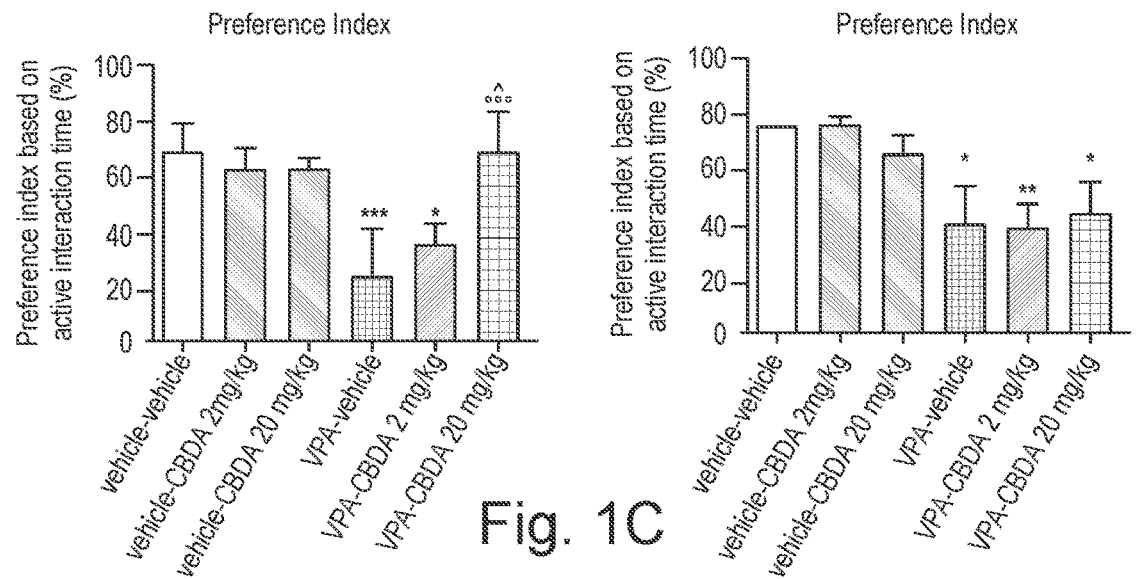

FIG. 1C shows the effect of CBDA treatment on the preference index in offspring of VPA- and vehicle-exposed rats, as measured through the three chamber apparatus. CBDA treatment at a dose of 20 mg/kg significantly counteracted the impairment in sociability observed in VPA treated rats. This effect was more noticeable in males than females.

Control rats spent significantly more time exploring the novel rat than the known rat ($p<0.01$). In contrast, VPA animals spent similar time exploring the two stimuli.

Figure 2A:
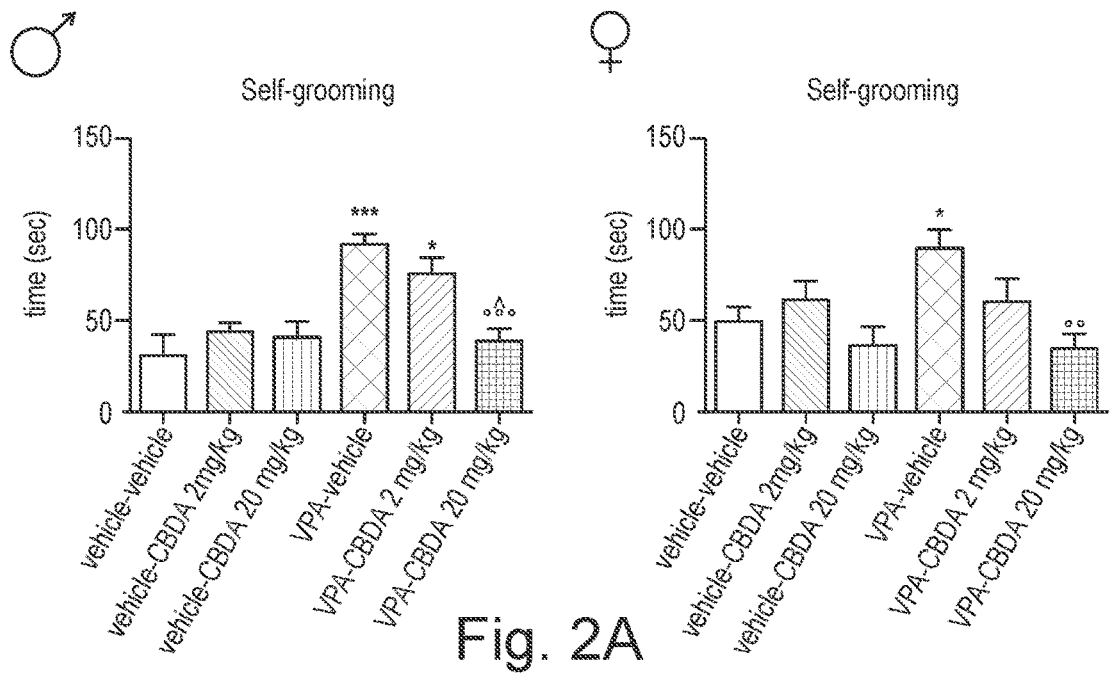
FIG. 2A-C shows the effect of CBDA on repetitive behaviours, hyperactivity, cognitive deficits and biomarkers in the rat VPA model of general autism.

FIG. 2A shows the effect of CBDA treatment on repetitive behaviours (compulsive self-grooming), in VPA-exposed offspring. Prenatal VPA exposure significantly increased the time spent in compulsive self-grooming by approximately 200% in males and 80% in females. CBDA administration at 20 mg/kg was able to significantly normalize this behaviour.

Figure 2B:
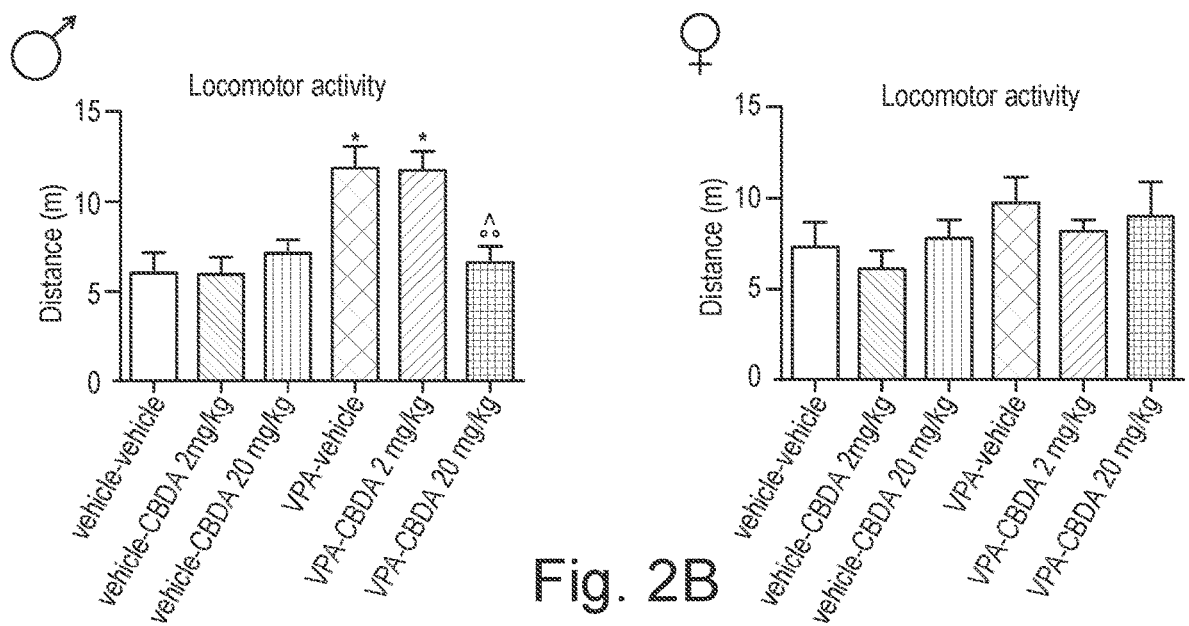

FIG. 2B shows the effect of CBDA treatment on locomotor activity in VPA offspring. VPA administration significantly increased locomotion by about 50% compared to control and CBDA administration at 20 mg/kg was able to normalize this.

Figure 2C:
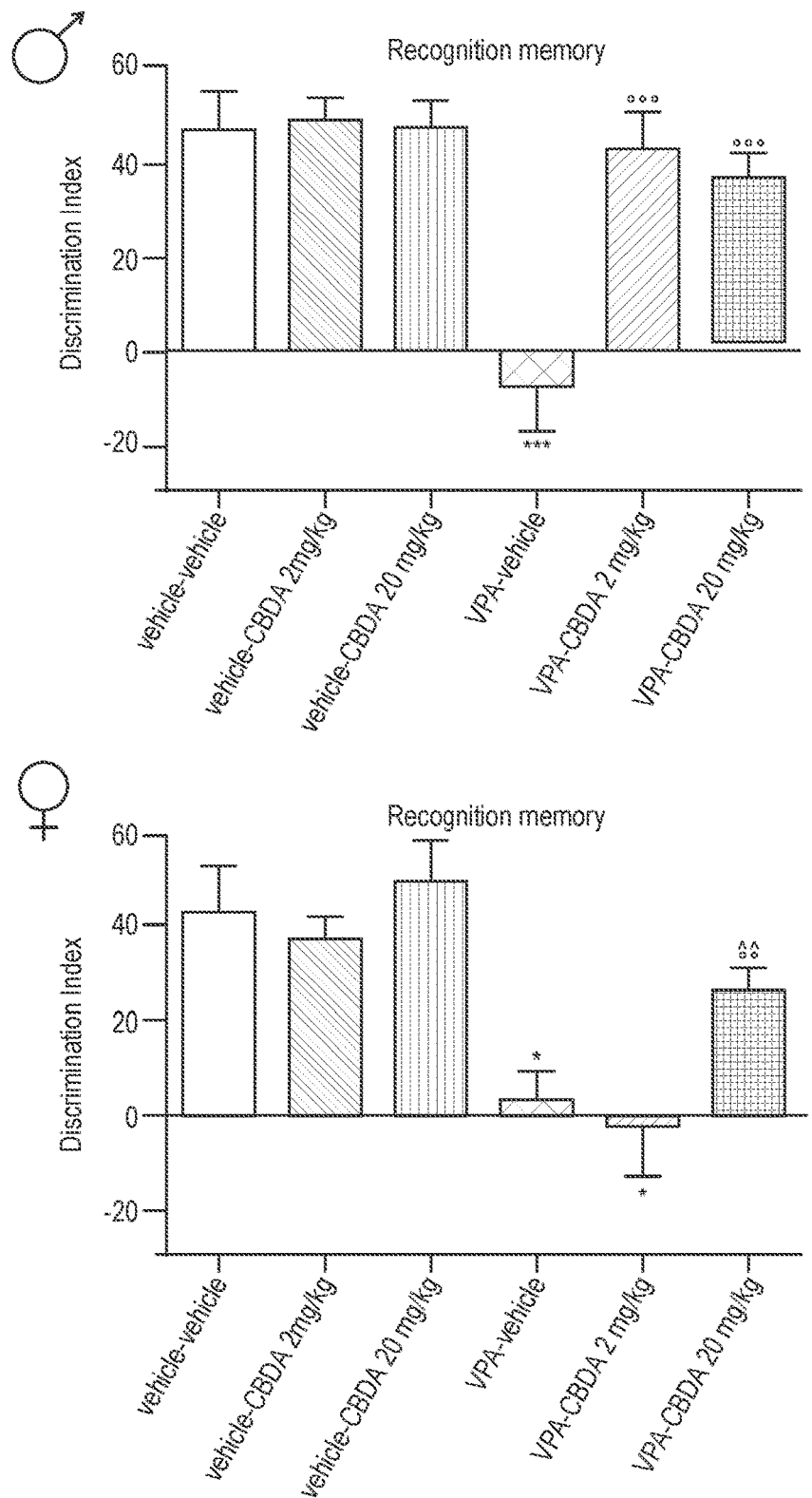

FIG. 2C shows the effect of CBDA treatment on short-term memory, evaluated through the novel object recognition test. Prenatal VPA administration significantly impaired short-term memory, as demonstrated by a significant reduction of the discrimination index by about 112% in male rats and 90% in female rats with respect to controls. CBDA at doses of 2 and 20 mg/kg completely and significantly reversed the short-term memory deficit in male and VPA rats, whereas CBDA at a dose of 20 mg/kg was able to reverse the short-term memory deficit in female VPA rats without affecting per se recognition memory when administered to vehicle-treated (non VPA) rats.

Conclusions

These data demonstrate that CBDA provided an effective treatment on the alterations in sociability, social novelty preference, short-term memory, repetitive behaviours and locomotion induced by prenatal VPA exposure offspring.

These data indicate that CBDA at doses of 2 and 20 mg/kg was able to reverse the autism-like phenotype in VPA-exposed rats and is therefore a potential novel treatment option for ASD.

Example 2

USe of Cannabidiolic Acid (CBDA) in a Mouse Model of Fragile X Syndrome

The phytocannabinoid cannabidiolic acid (CBDA) was evaluated in a mouse model of Fragile X syndrome (FXS). Such model evaluates the treatment on cognitive deficits and seizures present in Fmr1 knockout (KO) mice.

Materials and Methods
Animals

Fmr1 KO mice and wild type mice were obtained and housed four per cage in a temperature of 21° C.±1° C. and humidity of 55%±10% controlled environment. Food and water were available ad libitum. All experiments were performed during the light phase of a 12 hour light/dark cycle (08:00 to 20:00). Animals were handled for one week before the start of experiments. All behavioural tests were performed by researchers blind to the different experimental groups.

Novel Object Recognition Task

On day one mice were habituated for 10 minutes to the empty V-maze in which the task was to be performed. On the second day the mice went back to the maze for 10 minutes which contained two identical objects at the end of each corridor in the V-maze.

The following day the mice were placed again in the same maze for a further 10 minutes but one of the familiar objects was replaced for a novel object. The total time spent exploring the novel and familiar object was recorded. A discrimination index was calculated as the difference between the time spent exploring the novel and familiar object divided by the total time exploring the two objects. A high discrimination index (0.3-0.5) is considered to reflect memory retention for the familiar object.

Seizure Susceptibility

This trait was evaluated in PND21 mice after acute administration of the compounds or its vehicle, 30 min before starting the procedure. To measure audiogenic seizure sensitivity mice were placed individually into a novel environment, a glass cylinder (40 cm high, 16 cm diameter) and allowed to explore for 1 min. Next, a bell (100 dB) was rung for 30 sec and seizure activity scored according to the following scale: no response, 0; wild running, 1; clonic seizure, 2; tonic seizure, 3; status epilepticus/respiratory arrest/death, 4.

Experimental Protocol

Adult mice (10-15 weeks old) were treated either acutely with one dose of 20 mg/kg CBDA on PND 21 for 7 consecutive days. Mice were evaluated in the novel object recognition task after the first and sixth day of CBDA administration.

Results

Figure 3:
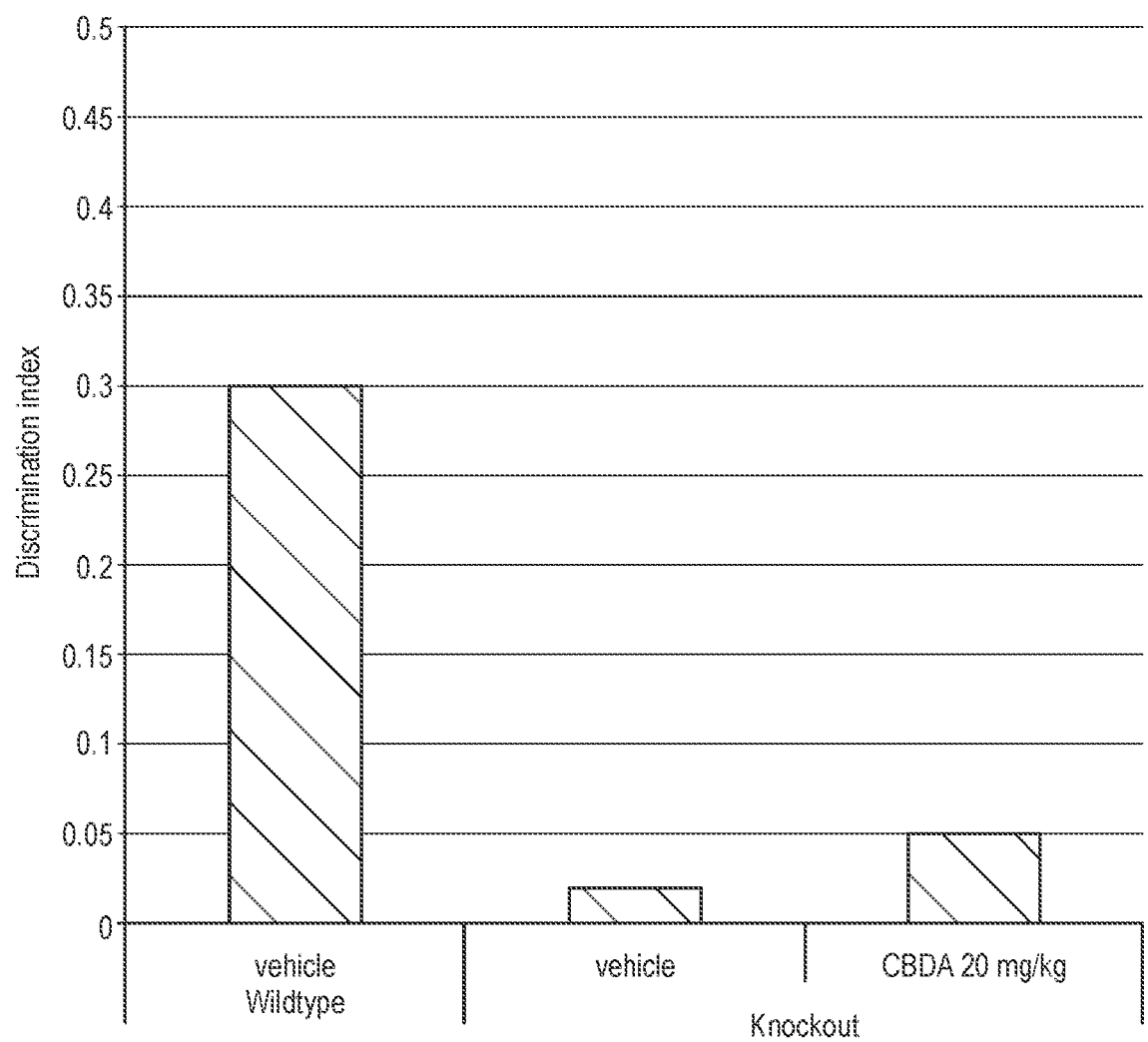
FIG. 3 shows the effect of CBDA on discrimination index after acute treatment in the mouse model of fragile X syndrome.

FIG. 3 shows the acute treatment of CBDA was able to increase the discrimination index slightly over that of the knockout mice administered vehicle, however this was not significant.

FIG. 4 demonstrates that after chronic treatment (once daily for 7 days) with CBDA there was a statistically significant increase in the discrimination index in the knockout mice over the vehicle treated knockout mice. The chronic treatment was able to completely restore the deficit in cognition experienced by the knockout mice.

The discrimination index level of 0.32 is considered to represent that the mice treated with CBDA over 7 days were able to retain memory for familiar objects in a similar manner to the wild type mice.

On postnatal day 21 (PND21) WT and Fmr1 KO mice were injected with CBDA (20 mg/kg) or vehicle, 30 min before exposure to a bell ring (100 dB). Mice exposed to this noise for 30 sec ceased from their normal exploratory behaviour and reacted with gradually to wild-running, clonic seizure, tonic seizure or death. The maximum response was annotated for each mouse as detailed in Table 2 below. A score was calculated according to the severity of the symptoms as explained in the Methods section.

As can be seen the FXS mice provided with CBDA experienced either no seizures or seizures of lower severity than those FXS mice dosed with vehicle. These data suggest that CBDA is able to reduce the seizure severity in FXS mice.

TABLE 2

Susceptibility to audiogenic seizures in Fmr1 KO and WT mice (PND21) after acute (30 min) administration of CBDV or vehicle

| WT | Vehicle n = 6 | CBDA (20 mg/kg) n = 6 |
|---|---|---|
| No response | 1 | 6 |
| Wild running | 5 | 0 |
| Clonic seizure | 0 | 0 |
| Tonic seizure | 0 | 0 |
| Death | 0 | 0 |

| FXS | Vehicle n = 6 | CBDA (20 mg/kg) n = 5 |
|---|---|---|
| No response | 0 | 2 |
| Wild running | 4 | 2 |
| Clonic seizure | 0 | 0 |
| Tonic seizure | 1 | 1 |
| Death | 1 | 0 |

Conclusions

These data demonstrate that the treatment with CBDA once daily for 7 days to mice which were deficient in the Fmr1 gene and subsequently suffered similar cognitive deficits to individuals with FXS, were able to reverse these cognitive deficits. Furthermore CBDA (20 mg/kg) was able to reduce the seizure severity in the FXS type mice.

As such CBDA is considered to be a viable treatment option for FXS.

Example 3

Use of Cannabidiolic Acid (CBDA) in a Mouse Model of Rett Syndrome

The phytocannabinoid cannabidivarin (CBDA) was evaluated in a mouse model of Rett syndrome (RS). Such model evaluates the treatment on motor alterations and cognitive deficits present in MeCP2 KO mice.

CBDA was administered daily at the dose of 2 or 20 mg/kg i.p. starting from PND 28 and the following signs were scored every other day: hindlimb clasping (indication of motor imbalance), tremor, gait (measure of coordination), breathing, mobility and general condition.

Furthermore, the efficacy of CBDA in reverting/attenuating the short- and long-term memory deficits present in these mice was evaluated. The Novel Object Recognition (NOR) test was performed before the starting of the treatment Post Natal Day 28 (PND 28), at PND 41 when the first motor symptoms appear and at PND 56 and 66 when the disease is fully manifested.

Materials and Methods

The CBDA was dissolved in ethanol, cremophor and saline (1:1:18). Starting from PND 28, mice received a daily intraperitoneal injection of CBDA (or vehicle) at the dose of 2 or 20 mg/kg. Animals were then scored every other day to evaluate the effect of CBDA treatment on motor symptoms (hindlimb clasping, gait, mobility) as well as neurological signs and general conditions (breathing abnormalities, tremors and general condition) present in MeCP2 knockout (KO) mice.

Symptom Scoring

Each of the six symptoms was scored from 0 to 2 (0 corresponds to the symptom being absent or the same as in the wild type (WT) animal; 1 when the symptom was present; 2 when the symptom was severe).

Mobility: the mouse is observed when placed on bench, then when handled gently. 0=as WT. 1=reduced movement when compared with WT: extended freezing period when first placed on bench and longer periods spent immobile. 2=no spontaneous movement when placed on the bench; mouse can move in response to a gentle prod or a food pellet placed nearby.

Gait: 0=as WT. 1=hind legs are spread wider than WT when walking or running with reduced pelvic elevation, resulting in a 'waddling' gait. 2=more severe abnormalities: tremor when feet are lifted, walks backward or 'bunny hops' by lifting both rear feet at once.

Hindlimb clasping: mouse observed when suspend by holding base of the tail. 0=legs splayed outward. 1=hindlimbs are drawn toward each other (without touching) or one leg is drawn into the body. 2=both legs are pulled in tightly, either touching each other or touching the body.

Tremor: mouse observed while standing on the flat palm of the hand. 0=no tremor. 1=intermittent mild tremor. 2=continuous tremor or intermittent violent tremor.

Breathing: movement of flanks observed while animal is standing still. 0=normal breathing. 1=periods of regular breathing interspersed with short periods of more rapid breathing or with pauses in breathing. 2=very irregular breathing-gasping or panting.

General condition: mouse observed for indicators of general well-being such as coat condition, eyes and body stance. 0=clean shiny coat, clear eyes, and normal stance. 1=eyes dull, coat dull/un-groomed, and somewhat hunched stance. 2=eyes crusted or narrowed, piloerection, and hunched posture.

At PND 28, 41, 56 and 66 the effect of CBDA on short- and long-term memory deficits was investigated through the Novel Object Recognition (NOR) test.

Novel Object Recognition (NOR) test

The experiment was performed as previously described (Zamberletti E. et al. 2014 and Kruk-Słomka M. et al. 2014).

The experimental apparatus used for the Novel Object Recognition test was an open-field box (43×43×32 cm) made of Plexiglas, placed in a dimly illuminated room. Animals performed each test individually.

Briefly, each animal was placed in the arena and allowed to explore two identical previously unseen objects for 10 minutes (familiarization phase). After an inter-trial interval of 30 minutes and 24 hours one of the two familiar objects was replaced by a novel, previously unseen object and mice were returned to the arena for the 10-minute test phase.

During the test phase the time spent exploring the familiar object (Ef) and the new object (En) was recorded separately by two observers blind to the groups and the discrimination index was calculated as follows: [(En−Ef)/(En+Ef)]×100.

Results

Figure 5A:
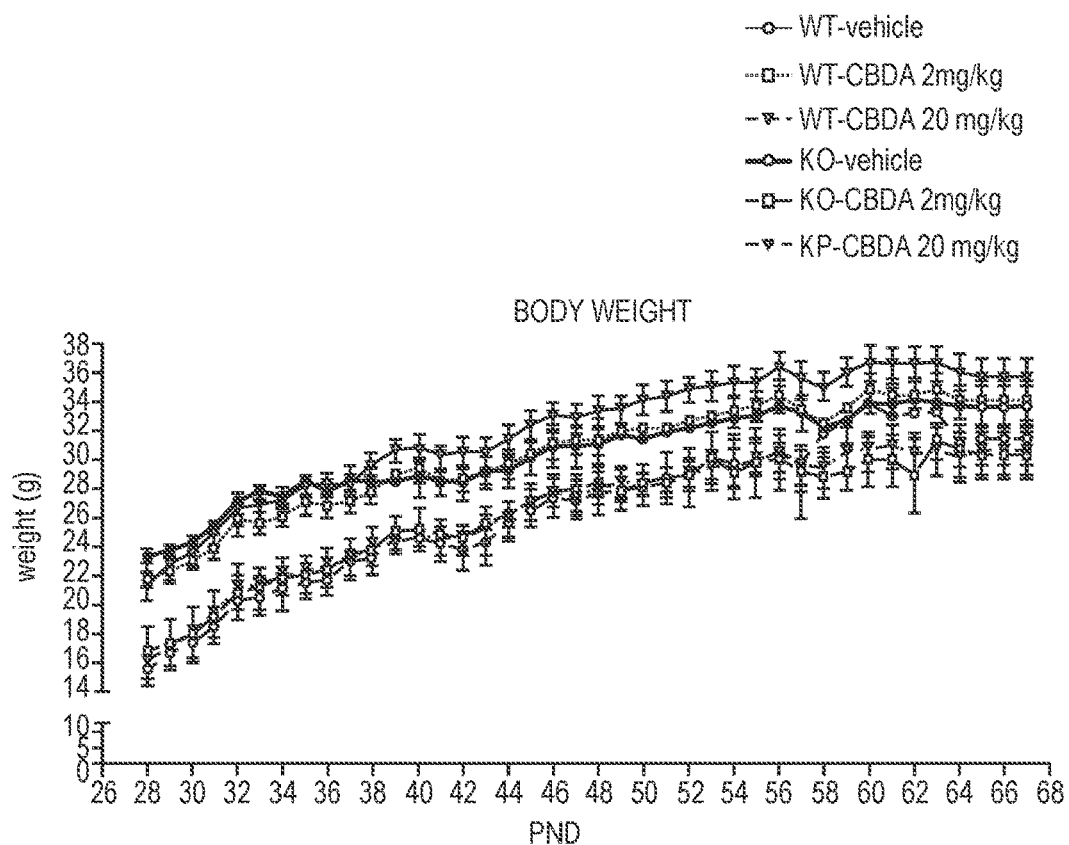
FIG. 5A-B shows the effect of CBDA on bodyweight in a mouse model of Rett syndrome.
Figure 5B:
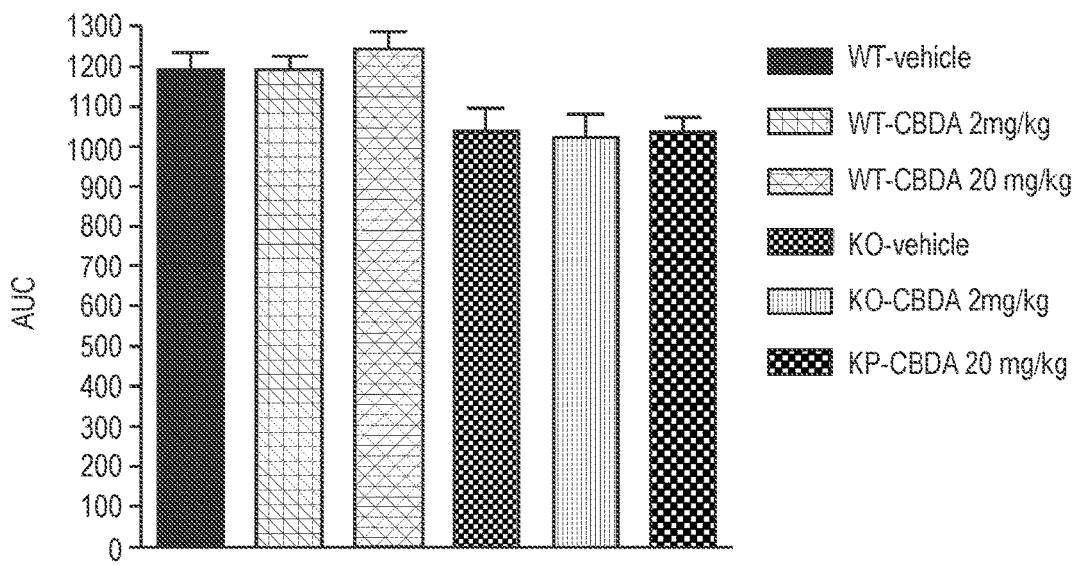

FIGS. 5A and 5B shows the effect of CBDA (2 and 20 mg/kg) on body weight gain in KO and wild type animals. Analysis of body weight gain as measured during the entire treatment period (PND 28-66) revealed that KO mice treated with vehicle were leaner than control wild type mice.

Treatment with CBDA at both doses did not prevent the reduction in body weight in the knockout mice.

Figure 6:
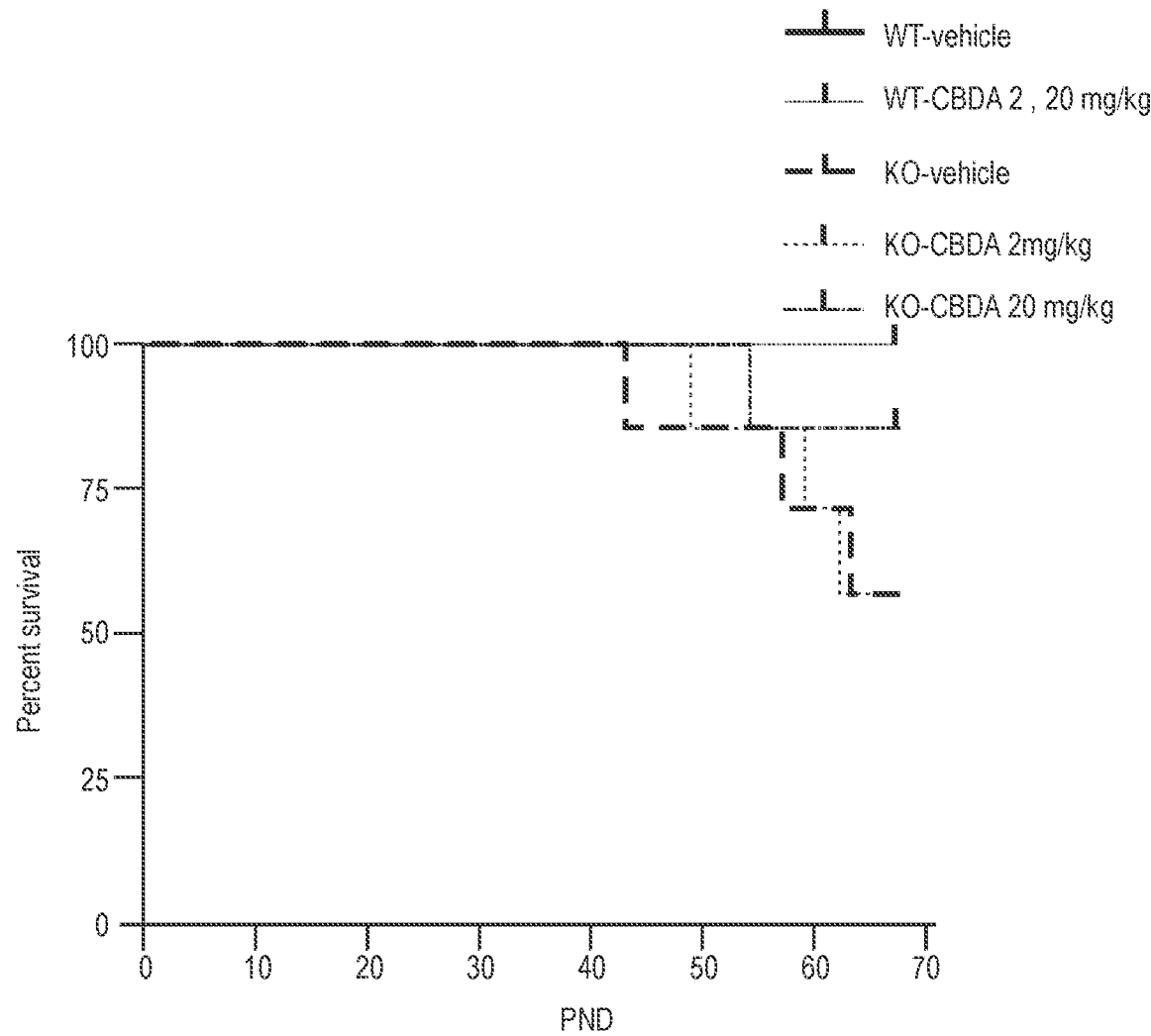
FIG. 6 shows the effect of CBDA on survival in a mouse model of Rett syndrome.

FIG. 6 shows the percentage of survival of MeCP2 KO and WT mice treated with two different doses of CBDA (2 and 20 mg/kg). The results are displayed as percent survival with respect to the time (PND).

No lethality was observed for WT mice treated with vehicle or CBDA. In contrast, survival in knockout mice treated with vehicle was 57.14% at PND 67. Chronic CBDA dosing at 20 mg/kg was able to increase the survival rate in knockout mice to 85.14%.

Figures 7A, 7B, 7C, 7D:
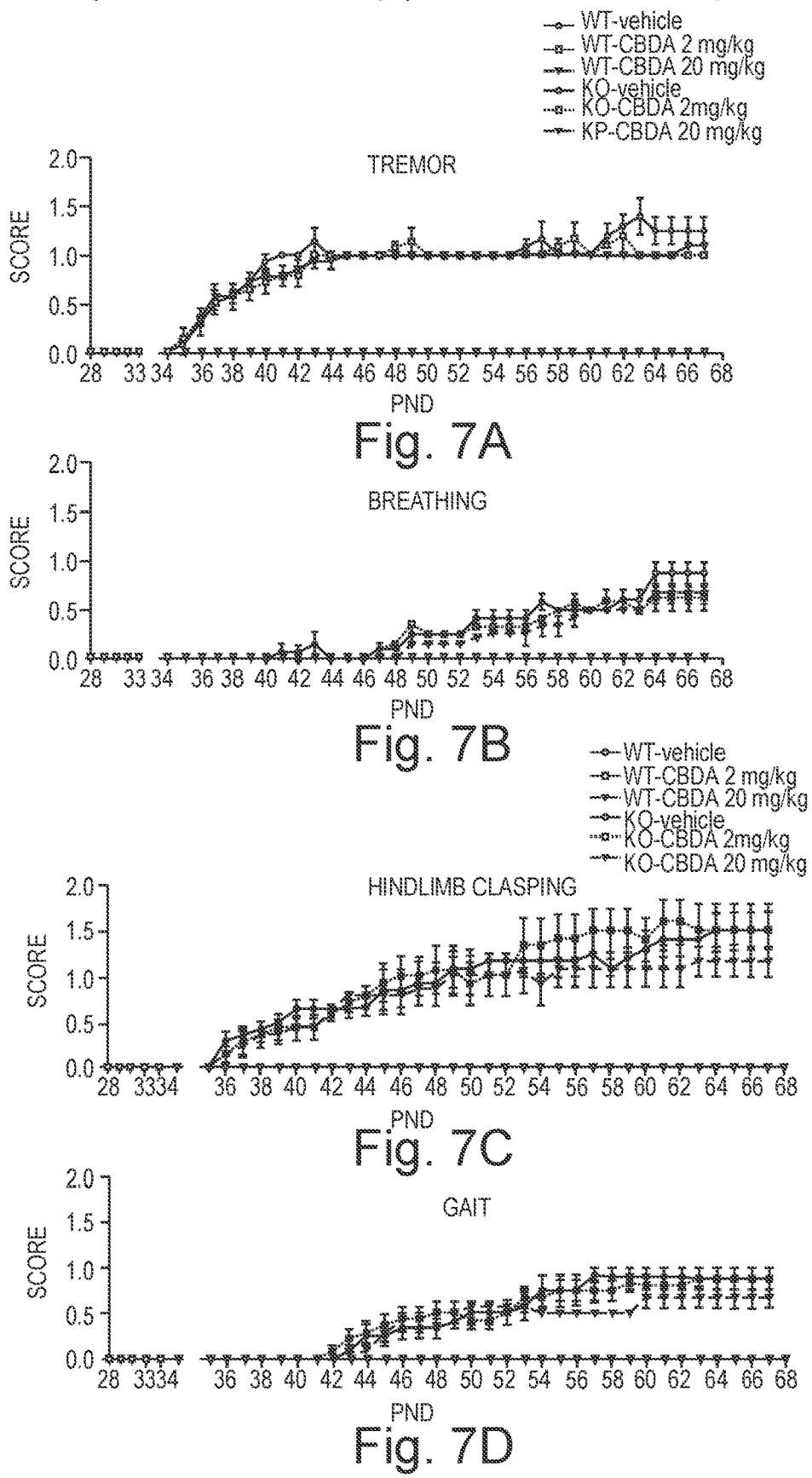
FIG. 7A-D shows the effect of CBDA on symptoms in a mouse model of Rett syndrome.
Figure 8A:
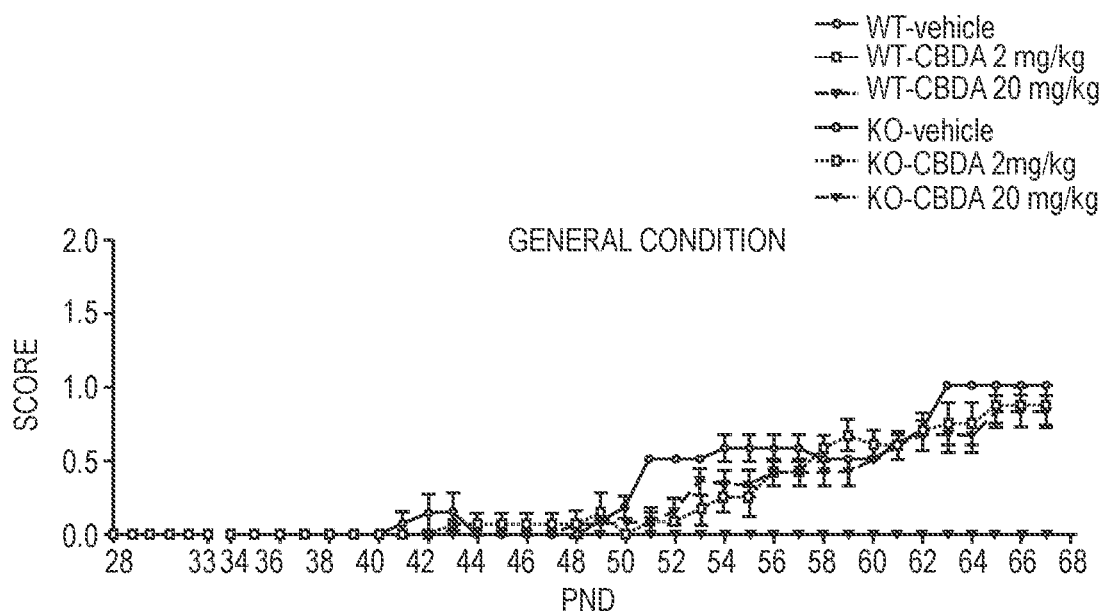
FIG. 8A-B shows the effect of CBDA on symptoms in a mouse model of Rett syndrome.
Figure 8B:
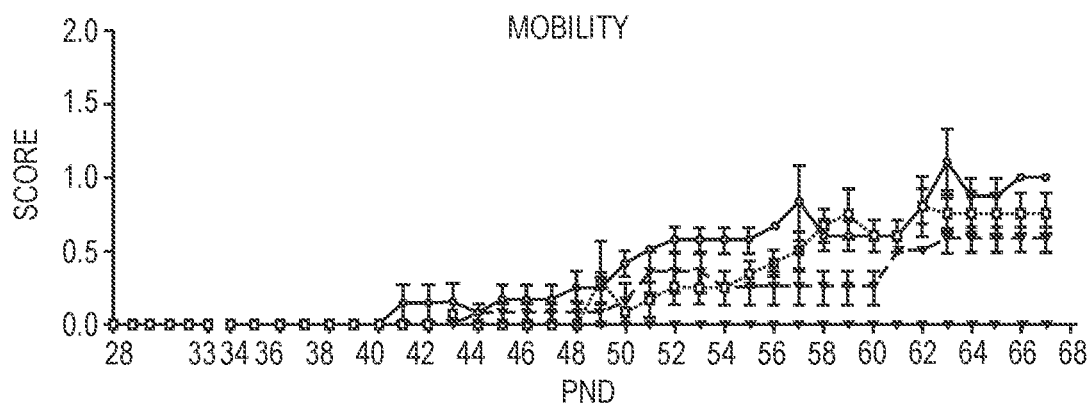

FIGS. 7 and 8 describes the effect of chronic CBDA (2 and 20 mg/kg) on six different signs of the phenotype (FIG. 7A tremor; 7B breathing; 7C hindlimb clasping; 7D gait, FIG. 8A general condition and 8B mobility) in KO mice at different stages of the disease.

Figure 9:
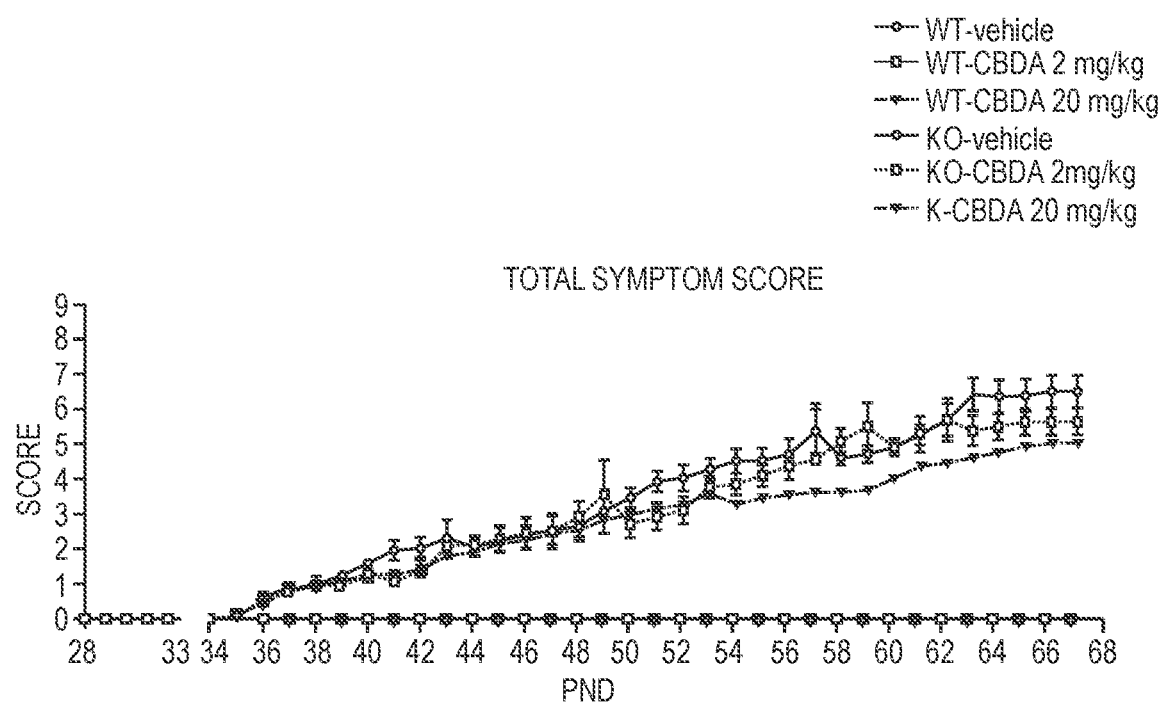
FIG. 9 shows the effect of CBDA on total symptom score in in a mouse model of Rett syndrome.

FIG. 9 describes how knockout mice showed an increase in these symptoms generally starting around PND35. Treatment with CBDA was able to partially improve these symptoms and decrease the total symptom score, however these data were not significant.

Figure 10:
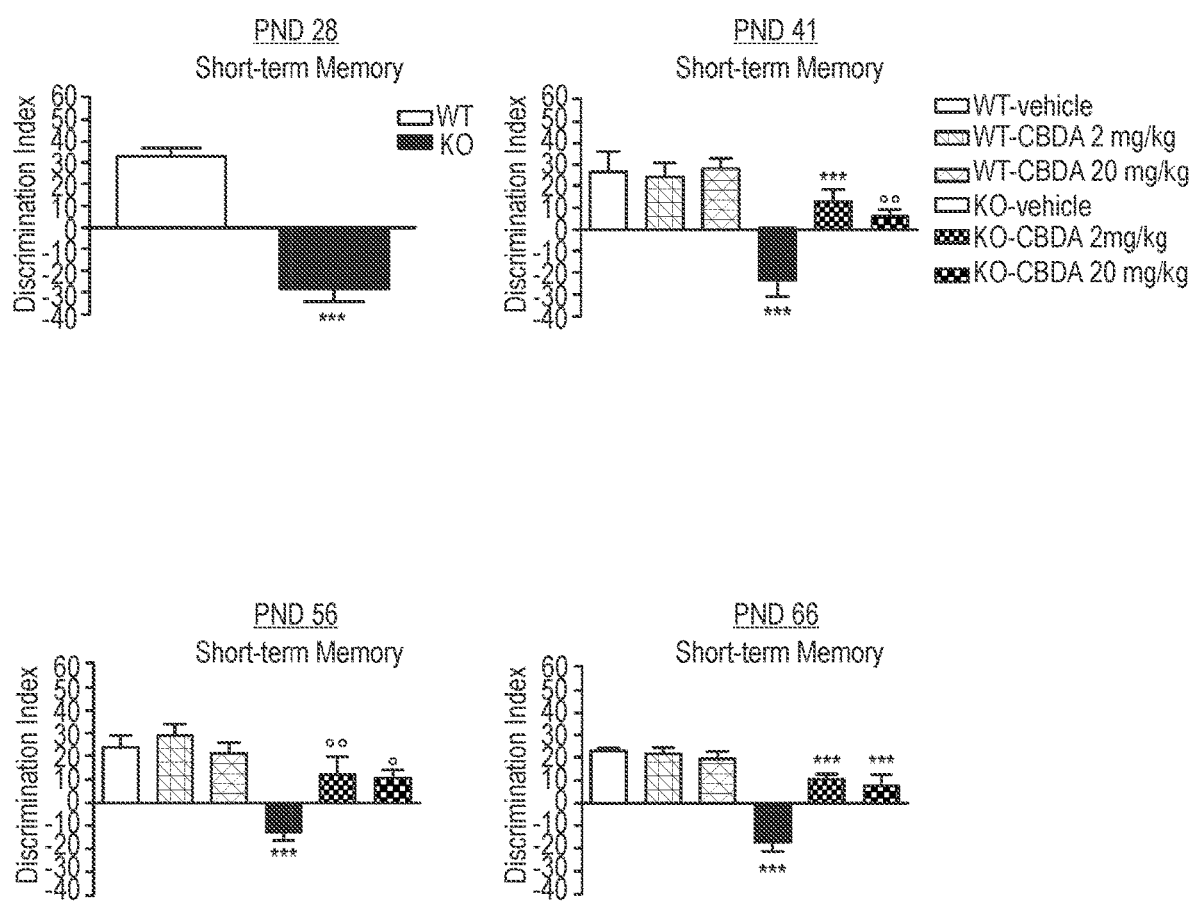
FIG. 10 shows the effect of CBDA on short-term memory in a mouse model of Rett syndrome.

FIG. 10 shows the effect of CBDA on short-term memory in the NOR test at different ages.

In KO animals, a significant cognitive impairment in short-term memory was found at PND 28, a time point when the motor symptoms are not present. This impairment was still present and significant at PND 41, 56 and 66, when the disease is fully manifested.

At each considered time point, administration of the two different doses of CBDA reverted the cognitive impairment in short-term memory present in KO mice without affecting recognition memory when administered to WT littermates.

Figure 11:
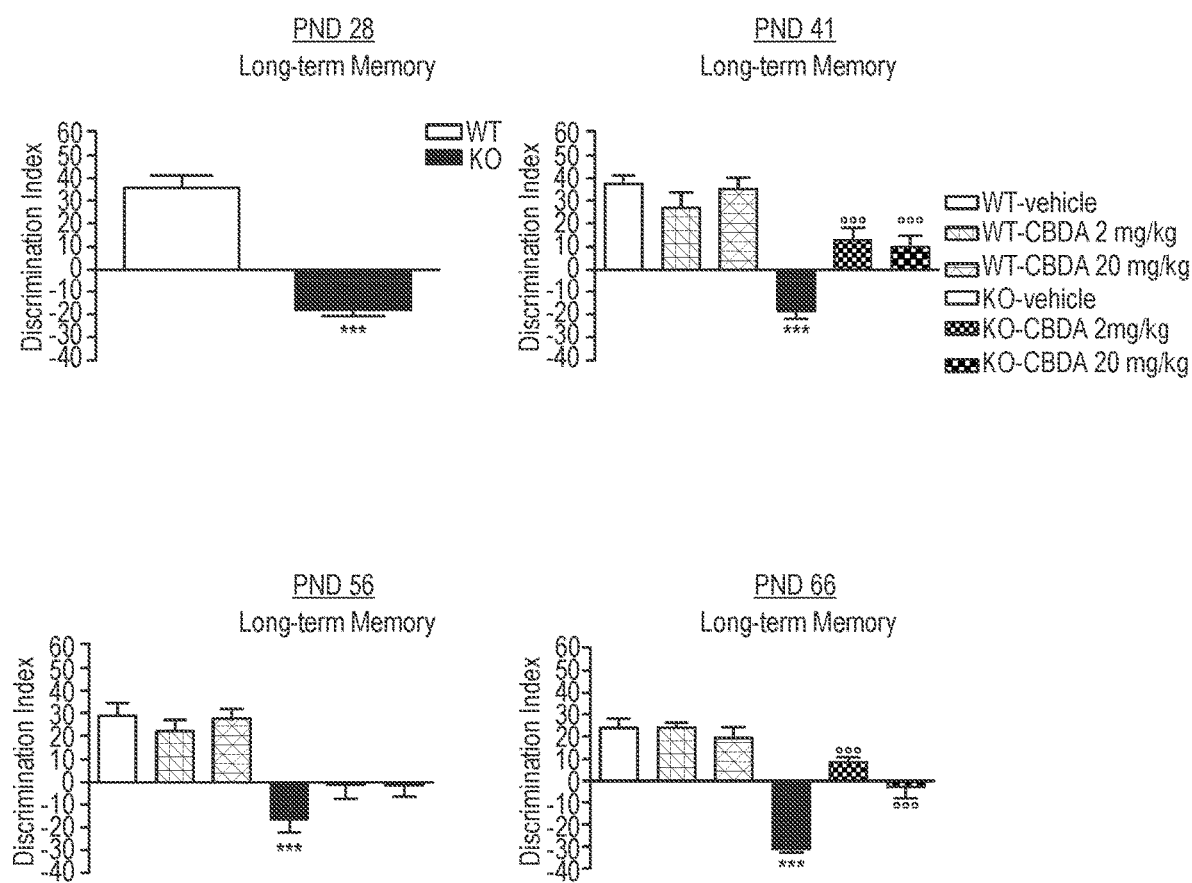
FIG. 11 shows the effect of CBDA on long-term memory in a mouse model of Rett syndrome.

FIG. 11 shows the effect of CBDA on long-term memory in the NOR test at different ages.

Similar to what has been observed for short-term memory; both doses of CBDA administered were also able to counteract the cognitive impairment in long-term memory present in KO mice without affecting recognition memory when administered to WT littermates.

Conclusions

These data demonstrate that CBDA treatment was effective in delaying and attenuating the phenotype of MeCP2 KO mice. The CBDA treatment was able to recover the deficits in short- and long-term memory present in those animals.

Importantly the survival rates in KO mice treated with CBDA was 85% in comparison to a survival rate of 57% in knockout mice treated with vehicle.

These data indicate that CBDA offers a significant treatment option in the treatment of RS.

Example 4

Use of Cannabidiolic Acid (CBDA) in a Mouse Model of Angelman Syndrome

The effect of CBDA was tested in the treatment of neurological, behavioural and motor disorders in a transgenic mouse model of Angelman Syndrome.

Materials and Methods

Animals

Heterozygous mice with maternal deficiency of Ube3A (Ube3am−/p+) and wild type (Ube3am+/p+) were purchased from The Jackson Laboratory (Jackson code: B6.129S7-Ube3a tm1Alb/J) and maintained in a C57BL/6 background.

Animals were housed under controlled illumination (12:12-hour light/dark cycle; light on 6 hours) and environmental conditions (room temperature: 20° C.-22° C., humidity: 55%-60%) with food and tap water were available ad libitum.

Drugs and Treatment

Drugs were dissolved in 1:1:18 ethanol:cremophor:0.9% saline, for intraperitoneal (i.p.) administration. Drug treatment was performed daily for 35 days. CBDA was administered at 20 mg/kg.

Behavioural Tests

Rotarod: The rotarod test assesses balance and motor coordination of mice. Mice have been measured for the time (in seconds) of equilibrium before falling on a rotary cylinder by a magnet that, activated from the fall of the mouse on the plate, allows to record the time of permanence on the cylinder. After a period of adaptation of 30 s, the spin speed gradually increased from 3 to 30 rpm for a maximum time of 5 min. The animals were analysed by 2 separate tests at 1-h interval in the same day.

Clasping: The clasping test assesses ataxia in mice. Mice were suspended by the base of the tail and their behaviours were recorded for 30 seconds. The time for which the mice clasped their hind limbs was recorded. The time was then scored as follows: 4, 15-30 s, 3, 10-15 s, 2, 5-10 s, 1, 0-5 s and 0,0 s Tail suspension: The tail suspension test assesses depressive-like behaviour in mice. Mice were individually suspended by the tail on a horizontal bar (50 cm from floor) using adhesive tape placed approximately 4 cm from the tip of the tail. The duration of immobility was recorded in seconds over a period of 6 minutes by a time recorder. Immobility time was defined as the absence of escape-oriented behaviour.

Novel Object Recognition: The novel object recognition assesses recognition memory in mice. The experiment started with the habituation period, during which mice were allowed to freely explore for 1 hour the apparatus which consists of a rectangular open box (40×30×30 cm width x length x height) made of grey polyvinyl chloride (PVC) illuminated by a dim light. The day after each mouse was allowed to explore two identical objects positioned in the back left and right corners for 5 min (acquisition). A video camera recorded the time spent on exploration of each object. In the test trial, which was carried out for 2 hrs after the acquisition, one of the two objects was replaced with a new different object. The time spent exploring the object was the time that the mouse spent with its nose directed and within 1 cm from the object. The behaviour of mice was analyzed by an observer blind to the treatment. Data are expressed as percentage of recognition index (RI %), which was calculated as the percentage of the time spent exploring the novel object/time spent exploring the novel object+time spent exploring the familiar object×100.

Statistical Analysis: Behavioural data are represented as means±SEM and statistical analysis of these data was performed by two way analysis of variance (ANOVA) for repeated measured followed by the Student Newman-Keuls for multiple comparisons to determine statistical significance between different treated groups of mouse. $p<0.05$ was considered statistically significant.

Results

Figure 12:
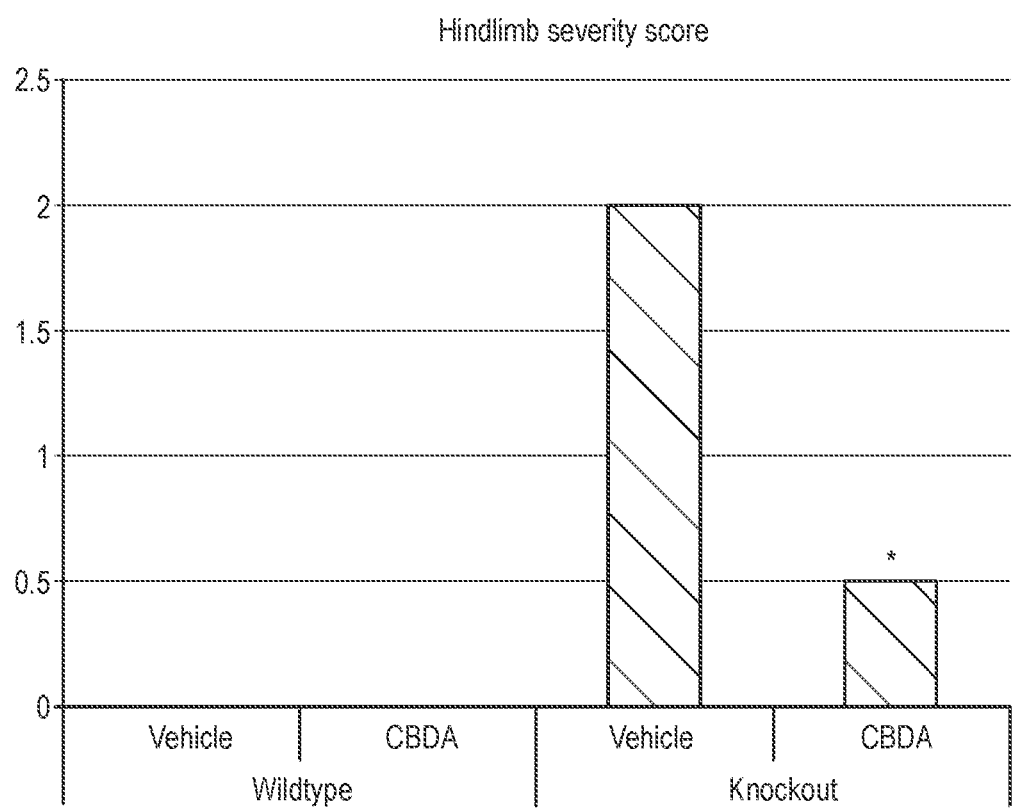
FIG. 12 shows the effect of CBDA on clasping duration in a mouse model of Angelman syndrome.

FIG. 12 shows that AS mice treated with vehicle showed significantly longer clasping duration at 10 weeks of age compared to WT mice treated with vehicle. In AS mice chronic treatment (30 days) with CBDA significantly reduced clasping duration at 10 weeks of age compared to AS mice treated with vehicle.

Figure 13:
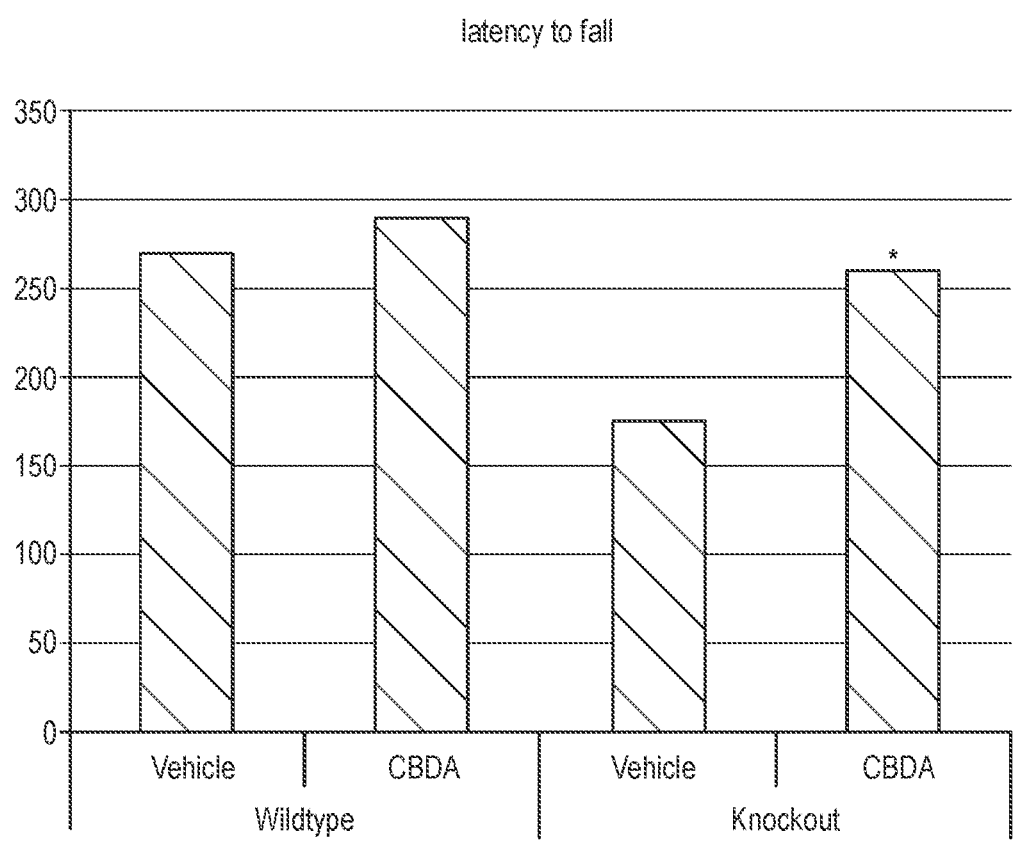
FIG. 13 shows the effect of CBDA in the rotarod test in a mouse model of Angelman syndrome.
Figure 14:
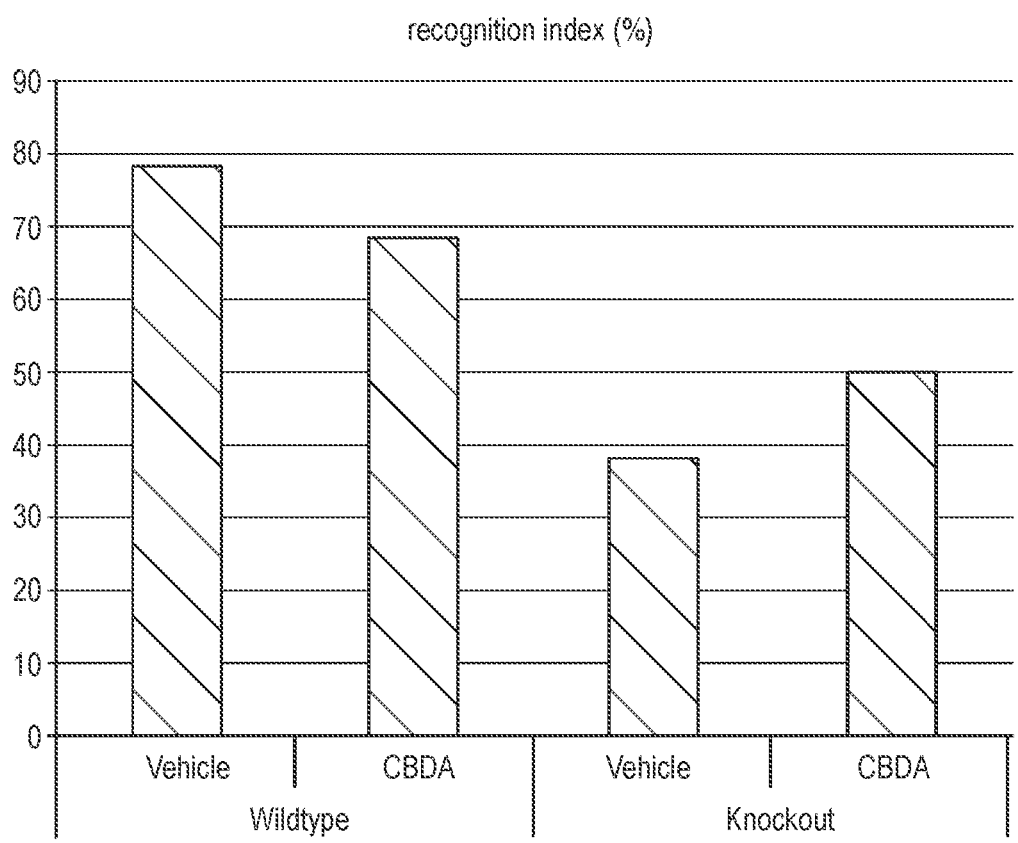
FIG. 14 shows the effect of CBDA in the novel object recognition test in a mouse model of Angelman syndrome.

FIG. 13 demonstrates that AS mice treated with vehicle showed a significant motor impairment at 10 weeks of compared to WT mice treated with vehicle. In AS mice, chronic treatment (30 days) with CBDA significantly reduced latency to fall compared to AS mice treated with vehicle.

Mice were assessed at the age of 7-8 weeks in the novel object recognition test. AS mice treated with vehicle showed a significant decrease in the discrimination index compared with WT mice that received the same treatment. FIG. 5 shows that AS mice treated with CBDA increased the discrimination index compared to AS mice treated with vehicle.

Figure 15:
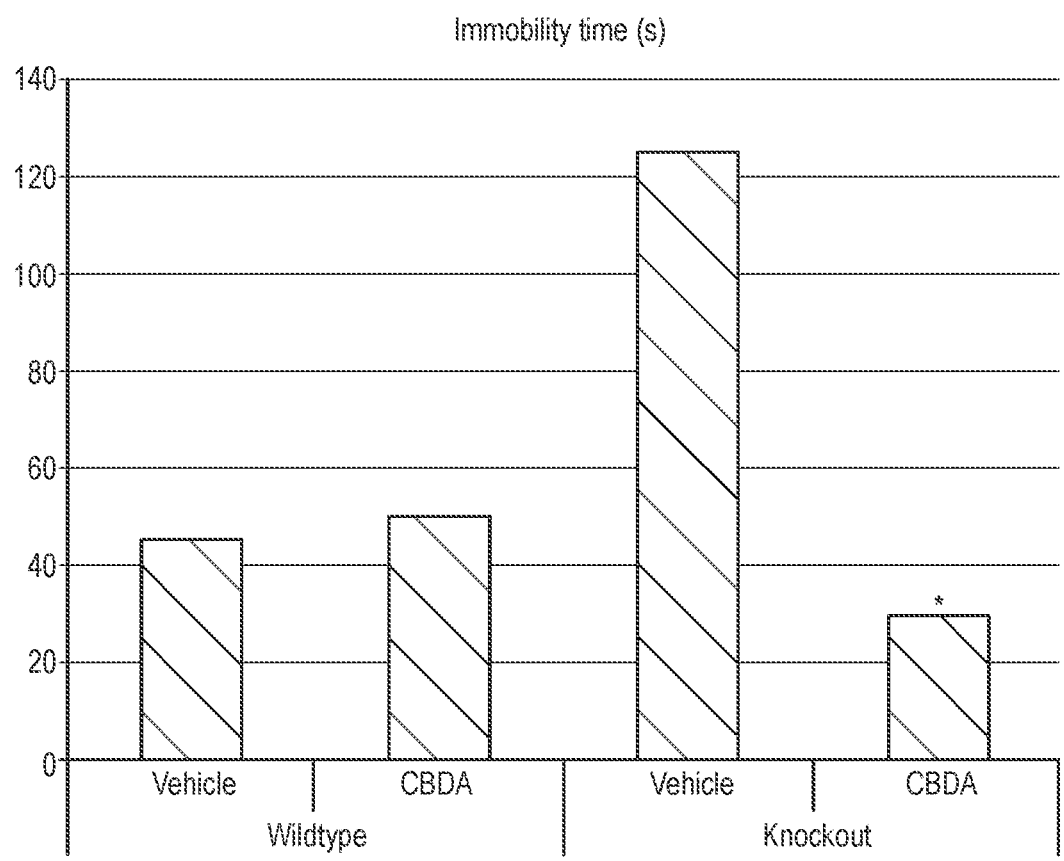
FIG. 15 shows the effect of CBDA in the tail suspension test in a mouse model of Angelman syndrome.

FIG. 15 shows that in the tail suspension test the time of immobility were significantly higher in AS mice that received vehicle compared to WT mice that received the same treatment. In AS mice treatment with CBDA significantly reduced the duration of immobility time compared to AS mice treated with vehicle.

Conclusion

These data demonstrate that the treatment of 20 mg/kg CBDA to mice which were deficient in the Ube3A gene and subsequently suffered similar cognitive deficits to individuals with AS, were able to reverse these cognitive deficits.

As such CBDA is considered to be a viable treatment option for AS.

Overall Conclusion

As is shown in Examples 1 to 4 above, the use of CBDA in a model of ASD and three different models of ASD-associated disorders is able to produce statistically significant reversal of the symptoms associated with these disorders.

In particular CBDA has been shown to produce positive results in the Novel Object Recognition (NOR) test in both models and as such demonstrates unequivocally that this phytocannabinoid could reverse cognitive dysfunction in these disorders.

In addition, other tests in these models provide support that CBDA could be used to treat additional symptoms associated with these disorders as it was able to reduce ataxia and anxiety symptoms in a model of Angelman syndrome. As such CBDA provides a real treatment option to individuals suffering from ASD, FXS, RS and AS.

REFERENCES

Hill T et al. (2012) Br J Pharmacol. December; 167(8):1629-42. Cannabidivarin is anticonvulsant in mouse and rat.

Erica Zamberletti, Sarah Beggiato, Luca Steardo Jr., Pamela Prini, Tiziana Antonelli, Luca Ferraro, Tiziana Rubino, Daniela Parolaro. Neurobiology of Disease (2014), Volume 63, Pages 35-47. "Alterations of prefrontal cortex GABAergic transmission in the complex psychotic-like phenotype induced by adolescent delta-9-tetrahydrocannabinol exposure in rats."

Kurz and Blass 2010 Use of dronabinol (delta-9-THC) in autism: A prospective single-case study with an early infantile autistic child. Cannabinoids, 5 (4) 4-6.

Marta Kruk-Słomka, Agnieszka Michalak, Barbara Budzyn'ska, Graz'yna Biala. Pharmacological Reports 66 (2014), 638-646. "A comparison of mecamylamine and bupropion effects on memory-related responses induced by nicotine and scopolamine in the novel object recognition test in mice."

The invention claimed is:

1. A method of treating one or more symptoms or disease characteristics associated with autistic spectrum disorder (ASD) or ASD-associated disorders, as defined by DSM-IV, in a subject in need thereof, the method comprising administering cannabidiolic acid (CBDA) to the subject, wherein the one or more symptoms or disease characteristics are one or more of: (i) qualitative impairment in social interaction; (ii) qualitative impairment in communication; and (iii) restricted repetitive and stereotyped patterns of behaviour interest and activities, wherein the CBDA is present as a highly purified extract of *cannabis* such that the CBDA is present at greater than 95% of the total extract (w/w).

2. The method according to claim 1, wherein the symptoms or disease characteristics of (i) qualitative impairment in social interaction include one or more of: (a) marked impairment in the use of multiple nonverbal behaviours; (b) failure to develop peer relationships appropriate to developmental level; (c) a lack of spontaneous seeking to share enjoyment, interests, or achievements with other people; and (d) lack of social or emotional reciprocity.

3. The method according to claim 1, wherein the symptoms or disease characteristics of (ii) qualitative impairment in communication include one or more of: (a) delay in, or total lack of, the development of spoken language (not accompanied by an attempt to compensate through alternative modes of communication such as gesture or mime); (b) in individuals with adequate speech, marked impairment in the ability to initiate or sustain a conversation with others; (c) stereotyped and repetitive use of language or idiosyncratic language; and (d) lack of varied, spontaneous make-believe play or social imitative play appropriate to developmental level.

4. The method according to claim 1, wherein the symptoms or disease characteristics of (iii) restricted repetitive and stereotyped patterns of behaviour interest and activities include one or more of: (a) encompassing preoccupation with one or more stereotyped and restricted patterns of interest that is abnormal either in intensity or focus; (b) apparently inflexible adherence to specific, non-functional routines or rituals; (c) stereotyped and repetitive motor mannerisms; and (d) persistent preoccupation with parts of objects.

5. The method according to claim 1, wherein the symptoms or disease characteristics associated with of autistic spectrum disorder comprise two or more symptoms associated with (i) qualitative impairment in social interaction; one or more symptoms associated with (ii) qualitative impairment in communication, and one or more symptoms associated with (iii) restricted repetitive and stereotyped patterns of behaviour interest and activities.

6. A method of treating one or more symptoms or disease characteristics associated with autistic spectrum disorder (ASD) or ASD-associated disorders, as defined by DSM-V, in a subject in need thereof, the method comprising administering cannabidiolic acid (CBDA) to the subject, wherein the one or more symptoms or disease characteristics are one or more of: (a) persistent deficits in social communication and social interaction across contexts, not accounted for by general developmental delays, and (b) restricted, repetitive patterns of behaviour, interests, or activities, wherein the CBDA is present as a highly purified extract of *cannabis* such that the CBDA is present at greater than 95% of the total extract (w/w).

7. The method according to claim 6, wherein the symptoms or disease characteristics of (a) persistent deficits in social communication and social interaction across contexts, not accounted for by general developmental delays include one or more of: (i) deficits in social-emotional reciprocity; (ii) deficits in nonverbal communicative behaviours used for social interaction; and (iii) deficits in developing and maintaining relationships.

8. The method according to claim 6, wherein the symptoms or disease characteristics of (b) restricted, repetitive patterns of behaviour, interests, or activities include one or more of: (i) stereotyped or repetitive speech, motor movements, or use of objects; excessive adherence to routines, (ii) ritualized patterns of verbal or nonverbal behaviour, or excessive resistance to change; (iii) highly restricted, fixated interests that are abnormal in intensity or focus; and (iv) hyper-or hypo-reactivity to sensory input or unusual interest in sensory aspects of environment.

9. The method according to claim 6 wherein the symptoms or disease characteristics associated with autistic spectrum disorder comprise all three of (i) deficits in social-emotional reciprocity; (ii) deficits in nonverbal communicative behaviours used for social interaction; and (iii) deficits in developing and maintaining relationships together with two or more of (i) stereotyped or repetitive speech, motor movements, or use of objects; excessive adherence to routines, (ii) ritualized patterns of verbal or nonverbal behaviour, or excessive resistance to change; (iii) highly restricted, fixated interests that are abnormal in intensity or focus; and (iv) hyper-or hypo-reactivity to sensory input or unusual interest in sensory aspects of environment.

10. The method according to claim 1, wherein the ASD-associated disorder is Fragile X syndrome.

11. The method according to claim 1, wherein the ASD-associated disorder is Rett syndrome.

12. The method according to claim 1, wherein the ASD-associated disorder is Angelman syndrome.

13. The method according to claim 1, wherein the CBDA is administered in combination with one or more concomitant medications.

14. The method according to claim 13, wherein the one or more concomitant medications is an anti-epileptic drug (AED), an anti-psychotic drug, melatonin, an SSRI, or methylphenidate.

15. The method according to claim 1, wherein the extract comprises less than 0.15% THC.

16. The method according to claim 1, wherein the dose of CBDA administered is greater than 0.01 mg/kg/day.

17. The method according to claim 16, wherein the dose of CBDA administered is between 1 to 30 mg/kg/day.

18. The method according to claim 1, wherein the CBDA is administered as an oral formulation.

* * * * *